US006638518B1

(12) United States Patent
Ratliff et al.

(10) Patent No.: US 6,638,518 B1
(45) Date of Patent: Oct. 28, 2003

(54) METHOD FOR INHIBITING INFLAMMATORY RESPONSES

(75) Inventors: Timothy L. Ratliff, Iowa City, IA (US); Joel N. Kline, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/510,031

(22) Filed: Feb. 22, 2000

Related U.S. Application Data

(60) Provisional application No. 60/121,177, filed on Feb. 22, 1999.

(51) Int. Cl.$^7$ .......................... A61K 45/00; A61K 39/00
(52) U.S. Cl. .............................. 424/282.1; 424/190.1; 424/192.1
(58) Field of Search ........................... 424/184.1, 185.1, 424/190.1, 234.1, 248.1, 278.1, 282.1, 192.1; 530/300, 350

(56) References Cited

U.S. PATENT DOCUMENTS

| | | | | |
|---|---|---|---|---|
| 4,716,038 | A | * | 12/1987 | Stanford et al. |
| 4,938,949 | A | | 7/1990 | Borch et al. |
| 5,618,916 | A | | 4/1997 | Ratliff et al. |
| 5,811,399 | A | * | 9/1998 | Khavinson et al. |
| 6,245,883 | B1 | * | 6/2001 | Heerze et al. |

FOREIGN PATENT DOCUMENTS

| | | | | |
|---|---|---|---|---|
| EP | 0322990 | | 7/1989 | ............ C07K/7/06 |
| WO | 95/25744 | * | 9/1995 | |
| WO | 97/23624 | | 7/1997 | ........... C12N/15/31 |
| WO | 99/37319 | * | 7/1999 | |

OTHER PUBLICATIONS

Kumar et al., "Murine model of chronic human asthma," *Immunology and Cell Biology.* 2001;79:141–144.

Lee et al., "Administration of interleukin–12 exerts a therapeutic instead of a long–term preventive effect on mite *Der p* I allergen–induced animal model of airway inflammation," *Immunology.* 1999;97:232–240.

Leong et al., "Understanding the pathogenesis of allergic asthma using mouse models," *Annals of Allergy, Asthma, & Immunology.* 2001;87:96–109.

Umland et al., "Effects of cyclosporin A and dinactin on T–cell proliferation, interleukin–5 production, and murine pulmonary inflammation," *Am. J. Respir. Cell Mol. Biol.* 1999;20:481–492.

Abou–Zeid et al., "Characterization of Fibronectin–Binding Antigens Released by *Mycobacterium tuberculosis* and *Mycobacterium bovis* BCG," *Infect. Immun.*, 56(12):3046–3051 (1988).

Aslanzadeh et al., "Characterization of Soluble Fibronectin Binding to Bacille Calmette–Guérin," *J. Gen. Microbiol.*, 135:2735–2741 (1989).

Ausubel, ed., *Current Protocols in Molecular Biology*, John Wiley & Sons, Inc., United States, Title page, publication page, and table of contents only, 12 pages (1994).

Beasley et al., "Cellular Events in the Bronchi in Mild Asthma and after Bronchial Provocation," *Am. Rev. Respir. Dis.*, 139(3):806–817 (1989).

Bliss et al., "IL–12, as an Adjuvant, Promotes a T Helper 1 Cell, but Does Not Suppress a T Helper 2 Cell Recall Response," *J. Immunol.*, 156(3):887–894 (1996).

Brosius et al., "Gene Organization and Primary Structure of a Ribosomal RNA Operon from *Escherichia coli*," *J. Mol. Biol.*, 148(2):107–127 (1981).

Bruijnzeel, "Eosinophil Tissue Mobilization in Allergic Disorders," *Cells and Cytokines in Lung Inflammation. Ann. NY Acad. Sci.*, 725:259–267 (1994).

Clutterbuck et al., "Human Interleukin 5 (IL–5) Regulates the Production of Eosinophils in Human Bone Marrow Cultures: Comparison and Interaction With IL–1. IL–3. IL–6 and GMCSF." *Blood*, 73(6):1504–1512 (1989).

Corrigan et al, "CD4 T–Lymphocyte Activation in Asthma is Accompanied by Increased Serum Concentrations of Interleukin 5 Effect of Glucocorticoid Therapy," *Ann. Rev. Respir. Dis.*, 147(3):540–547 (1993).

Del Prete et al., "Purified Protein Derivative of *Mycobacterium tuberculosis* and Excretory–Secretory Antigen(s) of *Toxocara canis* Expand in Vitro Human T Cells with Stable and Opposite (Type 1 T Helper or Type 2 T Helper) Profile of Cytokine Production," *J. Clin. Invest.*, 88, 346–350 (1991).

Erb et al., "Infection of Mice with *Mycobacterium bovis*–Bacillus Calmette–Guérin (BCG) Suppresses Allergen–induced Airway Eosinophilia," *J. Exp. Med.*, 187(4):561–569 (1998).

Evans et al., National Trends in the Morbidity and Mortality of Asthma in the U.S.; Prevalence, Hospitalization, and Death from Asthma Over Two Decades: 1965–184, *Chest*, 91(6):65S–74S (1987).

Field et al., "Evidence for Excessive Th2 CD4$^+$ Subset Activity in Vivo," *J. Immunol.*, 151(1):48–59 (1993).

Gajewski et al., "Anti–Proliferative Effect of IFN–γ in Immune Regulation. I. IFN–γ Inhibits the Proliferation of Th2 but Not Th1 Murine Helper T Lymphocyte Clones," *J. Immunol.*, 140(12):4245–4252 (1988).

(List continued on next page.)

Primary Examiner—Patricia A. Duffy
(74) Attorney, Agent, or Firm—Mueting, Raasch & Gebhardt, P.A.

(57) ABSTRACT

The present invention provides methods for treating at least one symptom of an inflammatory response in a mammal by administering a polypeptide to the mammal. The polypeptide can be a microbial polypeptide, or a Mycobacterial polypeptide. The present invention further provides an inflammation reaction inhibiting composition that includes a microbial polypeptide and a pharmaceutically acceptable carrier.

12 Claims, 11 Drawing Sheets

OTHER PUBLICATIONS

Grünig et al., "Requirement for IL–132 Independently of IL–4 in Experimental Asthma," *Science*, 282(5397):2261–2263 (1998).

Hirai et al., "Enhancement of Human Basophil Histamine Release by Interleukin 5," *J. Exp. Med.*, 172(4):1525–1528 (1990).

Hunter et al., "Isolation and characterization of the highly immunogenic cell wall–associated protein of *Mycobacterium leprae*," *J. Immunol.*, 142(8):2864–2872 (1989).

Jeffery et al., "Bronchial Biopsies in Asthma, An Ultrastructural Quantitative Study and Correlation with Hyperreactivity," *Am. Rev. Respir. Dis.*, 140:1745–1753 (1989).

Kavoussi et al., "Fibronectin–mediated Calmette–Guerin Bacillus Attachment to Murine Bladder Mucosa Requirement for the Expression of an Antitumor Response." *J. Clin. Invest.*, 85:62–67 (1990).

Kim et al., "Ribonuclease S–peptide as a carrier in fusion proteins," *Protein Sci.*, 2(2):348–356 (1993).

Kline et al., "*Mycobacterium bovis* BCG fibronectin attachment protein (FAP–B) prevents the development of airway eosinophilia and bronchial hyperreactivity in a murine model of asthma," Abstract and Poster, Ann. Meeting, Am. Thoracic Society, Apr., 1999, *Am. J. Respir. Crit. Care Med.*, 159, 21 pages (Apr., 1999).

Laitinen et al., "Damage of the Airway Epithelium and Bronchial Reactivity in Patients with Asthma," *Am. Rev. Respir. Dis.*, 131:599–606 (1985).

Laqueyrerie et al., "Cloning, Sequencing, and Expression of the *apa* Gene Coding for the *Mycobacterium tuberculosis* 45/47–Kilodalton Secreted Antigen Complex," *Infect. Immun.*, 63(10):4003–4010 (1995).

Lopez et al., "Recombinant human interleukin 5 is a selective activator of human eosinophil function," *J. Exp. Med.*, 167:219–223 (1988).

Marini et al., "Cytokine mRNA Profile and Cell Activation in Bronchoalveolar Lavage Fluid from Nonatopic Patients with Symptomatic Asthma," *Chest*, 102(3):661–669 (1992).

Metzger et al., "Late Asthmatic Responses: Inquiry into Mechanisms and Significance," *Clin. Rev. All.*, 3(2):145–165 (1985).

Metzger et al., "Bronchoalveolar Lavage of Allergic Asthmatic Patients following Allergen Bronchoprovocation," *Chest*, 89(4):477–483 (1986).

Metzger et al., "Local Allergen Challenge and Bronchoalveolar Lavage of Allergic Asthmatic Lungs: Description of the Model and Local Airway Inflammation," *Am. Rev. Respir. Dis.*, 135(2):433–440 (1987).

Micallef et al., "Interferon–γ–inducing factor enhances T helper 1 cytokine production by stimulated human T cells: synergism with interleukin–12 for interferon–γ production," *Eur. J. Immunol.*, 26:1647–1651 (1996).

Moore et al., "Homology of Cytokine Synthesis Inhibitory Factor (IL–10) to the Epstein–Barr Virus Gene BCRF1," *Science*, 248(4960):1230–1234 (1990).

Mosmann et al., "Two Types of Murine Helper T Cell Clone I. Definition According to Profiles of Lymphokine Activities and Secreted Proteins," *J. Immunol.*, 136(7):2348–2357 (1986).

National Asthma Education and Prevention Program, *Expert Panel Report 2: Guidelines for the Diagnosis and Management of Asthma*, National Institutes of Health, Bethesda, Md., 153 pages (1997).

O'Connor et al., "The Role of Allergy and Nonspecific Airway Hyperresponsiveness in the Pathogenesis of Chronic Obstructive Pulmonary Disease," *Am. Rev. Respir. Dis.*, 140(1):225–252 (1989).

Parronchi et al., "Allergen–and bacterial antigen–specific T–cell clones established from atopic donors show a different profile of cytokine production," *Proc. Natl. Acad. Sci. USA*, 88(10):4538–4542 (1991).

Parronchi et al., "IL–4 and IFN (αand γ) exert opposite regulatory effects on the development of cytolytic potential by Th1 or Th2 human T cell clones" *J. Immunol.*, 149(9):2977–2983 (1992).

Ratliff et al., "Attachment of Mycobacteria to Fibronectin–coated Surfaces," *J. Gen. Microbiol.*, 134(5):1307–1313 (1988).

Ratliff et al., "Purification of a Mycobacterial Adhesin for Fibronectin," *Infect. Immun.*, 61(5):1889–1894 (1993).

Robbins et al., *Pathologic Basis of Disease second edition*, W. B. Saunders Co., Philadelphia, Title page, publication page, and pages 689–692 (1979).

Robinson et al., "Predominant $T_{H2}$–like bronchoalveolar T–lymphocyte population in atopic asthma," *N. Engl. J. Med.*, 326(5):298–304 (1992).

Robinson et al., "Activation of $CD4^+$ T cells, increased $T_{H2}$–type cytokine mRNA expression, and eosinophil recruitment in bronchoalveolar lavage after allergen inhalation challenge in patients with atopic asthma," *J. All. Clin. Immunol.*, 92(2)313–324 (1993).

Robinson et al., "Relationships among numbers of bronchoalveolar lavage cells expressing messenger ribonucleic acid for cytokines, asthma symptoms, and airway methacholine responsiveness in atopic asthma," *J. All. Clin. Immunol.*, 92(3):397–403 (1993).

Romagnani, "Human $T_H1$ and $T_H2$ subsets: doubt no more," *Immunol. Today*, 12(8):256–257 (1991).

Romain et al., "Identification of a *Mycobacterium bovis* BCG 45/47–Kitodalton Antigen Complex, an Immunodominant Target for Antibody Response after Immunization with Living Bacteria," *Infect. Immun.*, 61(2):742–750 (1993).

Saito et al., "Selective differentiation and proliferation of hematopoietic cells induced by recombinant human interleukins," *Proc. Natl. Acad. Sci. USA*, 85(7):2288–2292 (1988).

Salgame et al., "Differing Lymphokine Profiles of Functional Subsets of Human CD4 and CD8 T Cell Clones," *Science*, 254(5029):279–282 (1991).

Sambrook et al., *Molecular Cloning, A Laboratory Manual*, Cold Spring Harbor Laboratory Press, Cold Spring Harbor, N.Y., Title page, publication page, and table of contents only, 30 pages (1989).

Schorey et al., "A *Mycobacterium leprae* Gene Encoding a Fibronectin Binding Protein Is Used for Efficient Invasion of Epithelial Cells and Schwann Cells," *Infect. Immun.*, 63(7):2652–2657 (1995).

Schorey et al., "Characterization of the fibronectin–attachment protein of *Mycobacterium avium* reveals a fibronectin–binding motif conserved among mycobacteria," *Mol. Microbiol.*, 21(2):321–329 (1996).

Sher et al., "Virulence of Six Strains of Mycobacterium bovis (BCG) in Mice," *Infect. Immun.*, 8(5):736–742 (1973).

Shirakawa et al., "The Inverse Association Between Tuberculin Responses and Atopic Disorder," *Science*, 275(5296):77–79 (1997).

Smith et al., "A National Estimate of the Economic Costs of Asthma," *Am. J. Respir. Crit. Care Med.,* 156(3):787–793 (1997).

Swain et al., "IL–4 directs the development of Th2–like helper effectors," *J. Immunol,* 145(11):3796–3806 (1990).

Takatsu et al., "Antigen–Induced T Cell–Replacing Factor (TRF) I. Functional Characterization of a TRF–Producing Helper T Cell Subset and Genetic Studies on TRF Production," *J. Immunol.,* 124(5):2414–2422 (1980).

Tatusova et al., "BLAST 2 Sequences, a new tool for comparing protein and nucleotide sequences," *FEMS Microbiol. Lett.,* 174(2):247–250 (1999).

Wakeham et al., "Lack of Both Types 1 and 2 Cytokines, Tissue Inflammatory Responses, and Immune Protection During Pulmonary Infection by *Mycobacterium bovis* Bacille Calmette–Guerin in IL–12–Deficient Mice," *J. Immunol.,* 160(12):6101–6111 (1998).

Walker et al., "Allergic and Nonallergic Asthmatics Have Distinct Patterns of T–Cell Activation and Cytokine Production in Peripheral Blood and Bronchoalveolar Lavage," *Am. Rev. Respir. Dis.,* 146(1):109–115 (1992).

Walsh et al., "IL–5 enhances the in vitro adhesion of human eosinophils but not neutrophils in a leucocyte integrin (CD 11/18)–dependent manner," *Immunol.,* 71:258–265 (1990).

Wierenga et al., "Evidence for compartmentalization of functional subsets of $CD4^+$ T lymphocytes in atopic patients," *J. Immunol.,* 144(12):4651–4656 (1990).

Wills–Karp et al., "Interleukin–13: Central Mediator of Allergic Asthma," *Science* 282(5397):2258–2261 (1998).

Zhao et al, "Characterization of the Fibronectin Binding Motif for a Unique Mycobacterial Fibronectin Attachment Protein FAP," *J. Biol. Chem.,* 274(8):4521–4526 (Feb., 1999; published on–line Feb. 19, 1999).

Zhao et al., "Role of a bacillus Calmette–Guerin fibronectin attachment protein in BCG–induced anti–tumor activity," *Int. J. Cancer,* 86(1):83–88 (Apr. 1, 2000).

* cited by examiner

SEQ ID NO: 1:
CACCCCACCAACACGCCAGTTCATGAGCCGACCCGCGCCGTCCTTGCGTCGCGCCGTTAA     60
<u>                                                   </u>
                                                   HpaI

```
SEQ ID NO: 2:    M  H  Q  V  D  P  N  L  T  R  R  K  G  R
              CACGGTAGGTTCTTCGCCATGCATCAGGTGGACCCCAACTTGACACGTCGCAAGGGACGA   120

L  A  A  L  A  I  A  A  M  A  S  A  S  L  V  T  V  A  V  P
              TTGGCGGCACTGGCTATCGCGGCGATGGCCAGCGCCAGCCTGGTGACCGTTGCGGTGCCC   180

A  T  A  N  A  D  P  E  P  A  P  P  V  P  T  T  A  A  S  P
              GCGACCGCCAACGCCGATCCGGAGCCAGCGCCCCCGGTACCCACAACGGCCGCCTCGCCG   240
                                              KpnI
               P  S  T  A  A  A  P  P  A  P  A  T  P  V  A  P  P  P  P  A
              CCGTCGACCGCTGCAGCGCCACCCGCACCGGCGACACCTGTTGCCCCCCCACCACCGGCC   300

A  A  N  T  P  N  A  Q  P  G  D  P  N  A  A  P  P  P  A  D
              GCCGCCAACACGCCGAATGCCCAGCCGGGCGATCCCAACGCAGCACCTCCGCCGGCCGAC   360

P  N  A  P  P  P  P  V  I  A  P  N  A  P  Q  P  V  R  I  D
              CCGAACGCACCGCCGCCACCTGTCATTGCCCCAAACGCACCCCAACCTGTCCGGATCGAC   420

N  P  V  G  G  F  S  F  A  L  P  A  G  W  V  E  S  D  A  A
              AACCCGGTTGGAGGATTCAGCTTCGCGCTGCCTGCTGGCTGGGTGGAGTCTGACGCCGCC   480

H  L  D  Y  G  S  A  L  L  S  K  T  T  G  D  P  P  F  P  G
              CACCTCGACTACGGTTCAGCACTCCTCAGCAAAACCACCGGGGACCCGCCATTTCCCGGA   540

Q  P  P  P  V  A  N  D  T  R  I  V  L  G  R  L  D  Q  K  L
              CAGCCGCCGCCGGTGGCCAATGACACCCGTATCGTGCTCGGCCGGCTAGACCAAAAGCTT   600

Y  A  S  A  E  A  T  D  S  K  A  A  A  R  L  G  S  D  M  G
              TACGCCAGCGCCGAAGCCACCGACTCCAAGGCCGCGGCCCGGTTGGGCTCGGACATGGGT   660

E  F  Y  M  P  Y  P  G  T  R  I  N  Q  E  T  V  S  L  D  A
              GAGTTCTATATGCCCTACCCGGGCACCCGGATCAACCAGGAAACCGTCTCGCTCGACGCC   720

N  G  V  S  G  S  A  S  Y  Y  E  V  K  F  S  D  P  S  K  P
              AACGGGGTGTCTGGAAGCGCGTCGTATTACGAAGTCAAGTTCAGCGATCCGAGTAAGCCG   780

N  G  Q  I  W  T  G  V  I  G  S  P  A  A  N  A  P  D  A  G
              AACGGCCAGATCTGGACGGGCGTAATCGGCTCGCCCGCGGCGAACGCACCGGACGCCGGG   840

P  P  Q  R  W  F  V  V  W  L  G  T  A  N  N  P  V  D  K  G
              CCCCCTCAGCGCTGGTTTGTGGTATGGCTCGGGACCGCCAACAACCCGGTGGACAAGGGC   900

A  A  K  A  L  A  E  S  I  R  P  L  V  A  P  P  P  A  P  A
              GCGGCCAAGGCGCTGGCCGAATCGATCCGGCCTTTGGTCGCCCCGCCGCCGGCGCCGGCA   960

P  A  P  A  E  P  A  P  A  P  A  P  A  G  E  V  A  P  T  P
              CCGGCTCCTGCAGAGCCCGCTCCGGCGCCGGCGCCGGCCGGGGAAGTCGCTCCTACCCCG   1020

T  T  P  T  P  Q  R  T  L  P  A
              ACGACACCGACACCGCAGCGGACCTTACCGGCCTGACCGGATCCGGCCGCACCCCAAGTG   1080

ATACCCCTGGGCGGGGTGTCAGCGCGGCCGGGCGCTCTTGAGC                   1123
```

*Fig. 1*

SEQUENCE LISTING

```
<160> NUMBER OF SEQ ID NOS: 8

<210> SEQ ID NO 1
<211> LENGTH: 1122
<212> TYPE: DNA
<213> ORGANISM: Mycobacterium bovis

<400> SEQUENCE: 1
caccccacca acacgccagt tcatgagccg acccgcgccg tccttgcgtc gcgccgttaa     60
cacggaggtt cttcgccatg catcaggtgg accccaactt gacacgtcgc aagggacgat    120
tggcggcact ggctatcgcg gcgatggcca gcgccagcct ggtgaccgtt gcggtgcccg    180
cgaccgccaa cgccgatccg gagccagcgc ccccggtacc cacaacggcc gcctcgccgc    240
cgtcgaccgc tgcagcgcca cccgcaccgg cgacacctgt tgcccccca ccaccggccg    300 ccgccaacac gccgaatgcc cagccgggcg atcccaacgc agcacctccg ccggccgacc    360
```

-continued

```
cgaacgcacc gccgccacct gtcattgccc caaacgcacc ccaacctgtc cggatcgaca    420
acccggttgg aggattcagc ttcgcgctgc ctgctggctg ggtggagtct gacgccgccc    480
acctcgacta cggttcagca ctcctcagca aaaccaccgg ggacccgcca tttcccggac    540
agccgccgcc ggtggccaat gacacccgta tcgtgctcgg ccggctagac caaaagcttt    600
acgccagcgc cgaagccacc gactccaagg ccgcggcccg gttgggctcg gacatgggtg    660
agttctatat gccctacccg ggcacccgga tcaaccagga aaccgtctcg ctcgacgcca    720
acggggtgtc tggaagcgcg tcgtattacg aagtcaagtt cagcgatccg agtaagccga    780
acggccagat ctggacgggc gtaatcggct cgcccgcggc gaacgcaccg gacgccgggc    840
cccctcagcg ctggtttgtg gtatggctcg ggaccgccaa caacccggtg gacaagggcg    900
cggccaaggc gctggccgaa tcgatccggc ctttggtcgc cccgccgccg gcgccggcac    960
cggctcctgc agagcccgct ccggcgccgg cgccggccgg ggaagtcgct cctaccccga   1020
cgacaccgac accgcagcgg accttaccgg cctgaccgga tccggccgca ccccaagtga   1080 taccoctggg cggggtgtca gcgcggccgg gcgctcttga gc                      1122
```

```

<210> SEQ ID NO 2
<211> LENGTH: 325
<212> TYPE: PRT
<213> ORGANISM: Mycobacterium bovis

<400> SEQUENCE: 2

Met His Gln Val Asp Pro Asn Leu Thr Arg Arg Lys Gly Arg Leu Ala
1               5                   10                  15

Ala Leu Ala Ile Ala Ala Met Ala Ser Ala Ser Leu Val Thr Val Ala
            20                  25                  30

Val Pro Ala Thr Ala Asn Ala Asp Pro Glu Pro Ala Pro Pro Val Pro
        35                  40                  45

Thr Thr Ala Ala Ser Pro Pro Ser Thr Ala Ala Ala Pro Pro Ala Pro
    50                  55                  60

Ala Thr Pro Val Ala Pro Pro Pro Pro Ala Ala Ala Asn Thr Pro Asn
65                  70                  75                  80

Ala Gln Pro Gly Asp Pro Asn Ala Ala Pro Pro Pro Ala Asp Pro Asn
                85                  90                  95

Ala Pro Pro Pro Pro Val Ile Ala Pro Asn Ala Pro Gln Pro Val Arg
            100                 105                 110

Ile Asp Asn Pro Val Gly Gly Phe Ser Phe Ala Leu Pro Ala Gly Trp
        115                 120                 125

Val Glu Ser Asp Ala Ala His Leu Asp Tyr Gly Ser Ala Leu Leu Ser
    130                 135                 140

Lys Thr Thr Gly Asp Pro Pro Phe Pro Gly Gln Pro Pro Pro Val Ala
145                 150                 155                 160

Asn Asp Thr Arg Ile Val Leu Gly Arg Leu Asp Gln Lys Leu Tyr Ala
                165                 170                 175

Ser Ala Glu Ala Thr Asp Ser Lys Ala Ala Ala Arg Leu Gly Ser Asp
            180                 185                 190

Met Gly Glu Phe Tyr Met Pro Tyr Pro Gly Thr Arg Ile Asn Gln Glu
        195                 200                 205

Thr Val Ser Leu Asp Ala Asn Gly Val Ser Gly Ser Ala Ser Tyr Tyr
    210                 215                 220

Glu Val Lys Phe Ser Asp Pro Ser Lys Pro Asn Gly Gln Ile Trp Thr
225                 230                 235                 240
```

-continued

```
Gly Val Ile Gly Ser Pro Ala Ala Asn Ala Pro Asp Ala Gly Pro Pro
                245                 250                 255

Gln Arg Trp Phe Val Val Trp Leu Gly Thr Ala Asn Asn Pro Val Asp
            260                 265                 270

Lys Gly Ala Ala Lys Ala Leu Ala Glu Ser Ile Arg Pro Leu Val Ala
        275                 280                 285

Pro Pro Pro Ala Pro Ala Pro Ala Pro Ala Glu Pro Ala Pro Ala Pro
    290                 295                 300

Ala Pro Ala Gly Glu Val Ala Pro Thr Pro Thr Thr Pro Thr Pro Gln
305                 310                 315                 320

Arg Thr Leu Pro Ala
                325

<210> SEQ ID NO 3
<211> LENGTH: 42
<212> TYPE: PRT
<213> ORGANISM: Artificial Sequence
<220> FEATURE:
<223> OTHER INFORMATION: VECTOR-ENCODED AMINO TERMINAL DOMAIN

<400> SEQUENCE: 3

Met Gly Gly Ser His His His His His His Gly Met Ala Ser Met Thr
1               5                   10                  15

Gly Gly Gln Gln Met Gly Arg Asp Leu Tyr Asp Asp Asp Lys His Arg
            20                  25                  30

Trp Ile Arg Pro Arg Asp Leu Gln Leu Val
        35                  40

<210> SEQ ID NO 4
<211> LENGTH: 287
<212> TYPE: PRT
<213> ORGANISM: Mycobacterium leprae

<400> SEQUENCE: 4

Met Asn Gln Val Asp Leu Asp Ser Thr His Arg Lys Gly Leu Trp Ala
1               5                   10                  15

Ile Leu Ala Ile Ala Val Val Ala Ser Ala Ser Ala Phe Thr Met Pro
            20                  25                  30

Leu Pro Ala Ala Ala Asn Ala Asp Pro Ala Pro Leu Pro Pro Ser Thr
        35                  40                  45

Ala Thr Ala Ala Pro Ser Pro Ala Gln Glu Ile Ile Thr Pro Leu Pro
    50                  55                  60

Gly Ala Pro Val Ser Ser Glu Ala Gln Pro Gly Asp Pro Asn Ala Pro
65                  70                  75                  80

Ser Leu Asp Pro Asn Ala Pro Tyr Pro Leu Ala Val Asp Pro Asn Ala
                85                  90                  95

Gly Arg Ile Thr Asn Ala Val Gly Gly Phe Ser Phe Val Leu Pro Ala
            100                 105                 110

Gly Trp Val Glu Ser Glu Ala Ser His Leu Asp Tyr Gly Ser Val Leu
        115                 120                 125

Leu Ser Lys Ala Ile Glu Gln Pro Pro Val Leu Gly Gln Pro Thr Val
    130                 135                 140

Val Ala Thr Asp Thr Arg Ile Val Leu Gly Arg Leu Asp Gln Lys Leu
145                 150                 155                 160

Tyr Ala Ser Ala Glu Ala Asp Asn Ile Lys Ala Ala Val Arg Leu Gly
                165                 170                 175
```

-continued

Ser Asp Met Gly Glu Phe Tyr Leu Pro Tyr Pro Gly Thr Arg Ile Asn
180 185 190

Gln Glu Thr Ile Pro Leu His Ala Asn Gly Ile Ala Gly Ser Ala Ser
195 200 205

Tyr Tyr Glu Val Lys Phe Ser Asp Pro Asn Lys Pro Ile Gly Gln Ile
210 215 220

Cys Thr Ser Val Val Gly Ser Pro Ala Ala Ser Thr Pro Asp Val Gly
225 230 235 240

Pro Ser Gln Arg Trp Phe Val Val Trp Leu Gly Thr Ser Asn Asn Pro
245 250 255

Val Asp Lys Gly Ala Ala Lys Glu Leu Ala Glu Ser Ile Arg Ser Glu
260 265 270

Met Ala Pro Ile Pro Ala Ser Val Ser Ala Pro Ala Pro Val Gly
275 280 285

<210> SEQ ID NO 5
<211> LENGTH: 381
<212> TYPE: PRT
<213> ORGANISM: Mycobacterium avium

<400> SEQUENCE: 5

Met Asp Gln Val Glu Ala Thr Ser Thr Arg Arg Lys Gly Leu Trp Thr
1 5 10 15

Thr Leu Ala Ile Thr Thr Val Ser Gly Ala Ser Ala Val Val Ile Ala
20 25 30

Leu Pro Glu Thr Ser His Ala Asp Pro Glu Val Pro Thr Pro Val Pro
35 40 45

Pro Ser Thr Ala Thr Thr Pro His Pro Arg Arg Arg Arg Ile Pro Gly
50 55 60

Gln Pro Ala Asp Asn Ala Gln Ala Gly Ala Pro Ala Pro Ala Pro Asn
65 70 75 80

Gly Gln Gln Arg Pro Pro Arg Arg Arg Arg Met Ile Pro Thr Arg Ala
85 90 95

Pro Pro Pro Ala Gly Ala Pro Pro Asn Gly Ala Pro Pro Ala Ala Pro
100 105 110

Asn Gly Ala Pro Pro Pro Pro Val Asp Pro Asn Ala Pro Pro Pro Pro
115 120 125

Pro Ala Asp Pro Asn Ala Gly Arg Ile Pro Asn Ser Tyr Val Leu Pro
130 135 140

Ala Gly Trp Val Glu Ser Asp Ala Ser His Leu Asp Tyr Gly Ser Ala
145 150 155 160

Leu Leu Ser Lys Val Thr Gly Pro Pro Pro Met Pro Asp Gln Pro Pro
165 170 175

Pro Val Ala Asn Asp Thr Arg Ile Val Met Gly Arg Val Asp Gln Lys
180 185 190

Leu Tyr Ala Ser Ala Glu Ala Asn Asn Ala Lys Ala Ala Val Gly Leu
195 200 205

Gly Ser Asp Met Gly Glu Phe Phe Met Pro Tyr Pro Gly Thr Arg Ile
210 215 220

Asn Gln Asp Ser Thr Pro Leu Asn Gly Ala Asn Gly Ser Thr Gly Ser
225 230 235 240

Ala Ser Tyr Tyr Glu Val Lys Phe Ser Asp Ala Ser Lys Pro Asn Gly
245 250 255

Gln Ile Trp Thr Gly Val Ile Gly Ser Ala Asn Ala Gly Asn Arg Gln
260 265 270

-continued

```
Arg Trp Phe Val Val Trp Leu Gly Thr Ser Asn Asp Pro Val Asp Lys
        275                 280                 285

Val Ala Ala Lys Ala Leu Ala Glu Ser Ile Gln Ala Trp Thr Pro Pro
    290                 295                 300

Pro Ala Pro Pro Ala Ala Pro Gly Gly Pro Gly Ala Pro Ala Pro Gly
305                 310                 315                 320

Ala Pro Gly Ala Pro Ala Pro Gly Ala Pro Ala Pro Gly Val Thr
            325                 330                 335

Ala Pro Ala Ala Pro Ala Pro Ala Ala Pro Gly Ala Pro Ala Ala Pro
        340                 345                 350

Gly Ala Pro Ala Pro Glu Pro Gly Gln Ala Pro Ala Val Glu Val Ser
        355                 360                 365

Pro Thr Pro Thr Pro Thr Pro Gln Gln Thr Leu Ser Ala
        370                 375                 380

<210> SEQ ID NO 6
<211> LENGTH: 325
<212> TYPE: PRT
<213> ORGANISM: Mycobacterium tuberculosis

<400> SEQUENCE: 6

Met His Gln Val Asp Pro Asn Leu Thr Arg Arg Lys Gly Arg Leu Ala
1               5                   10                  15

Ala Leu Ala Ile Ala Ala Met Ala Ser Ala Ser Leu Val Thr Val Ala
            20                  25                  30

Val Pro Ala Thr Ala Asn Ala Asp Pro Glu Pro Ala Pro Pro Val Pro
        35                  40                  45

Thr Thr Ala Ala Ser Pro Pro Ser Thr Ala Ala Ala Pro Pro Ala Pro
    50                  55                  60

Ala Thr Pro Val Ala Pro Pro Pro Ala Ala Ala Asn Thr Pro Asn
65                  70                  75                  80

Ala Gln Pro Gly Asp Pro Asn Ala Ala Pro Pro Ala Asp Pro Asn
            85                  90                  95

Ala Pro Pro Pro Val Ile Ala Pro Asn Ala Pro Gln Pro Val Arg
            100                 105                 110

Ile Asp Asn Pro Val Gly Gly Phe Ser Phe Ala Leu Pro Ala Gly Trp
        115                 120                 125

Val Glu Ser Asp Ala Ala His Phe Asp Tyr Gly Ser Ala Leu Leu Ser
    130                 135                 140

Lys Thr Thr Gly Asp Pro Pro Phe Pro Gly Gln Pro Pro Val Ala
145                 150                 155                 160

Asn Asp Thr Arg Ile Val Leu Gly Arg Leu Asp Gln Lys Leu Tyr Ala
                165                 170                 175

Ser Ala Glu Ala Thr Asp Ser Lys Ala Ala Arg Leu Gly Ser Asp
            180                 185                 190

Met Gly Glu Phe Tyr Met Pro Tyr Pro Gly Thr Arg Ile Asn Gln Glu
        195                 200                 205

Thr Val Ser Leu Asp Ala Asn Gly Val Ser Gly Ser Ala Ser Tyr Tyr
    210                 215                 220

Glu Val Lys Phe Ser Asp Pro Ser Lys Pro Asn Gly Gln Ile Trp Thr
225                 230                 235                 240

Gly Val Ile Gly Ser Pro Ala Ala Asn Ala Pro Asp Ala Gly Pro Pro
                245                 250                 255

Gln Arg Trp Phe Val Val Trp Leu Gly Thr Ala Asn Asn Pro Val Asp
            260                 265                 270
```

-continued

Lys Gly Ala Ala Lys Ala Leu Ala Glu Ser Ile Arg Pro Leu Val Ala
            275                 280                 285

Pro Pro Pro Ala Pro Ala Pro Ala Pro Glu Pro Ala Pro Ala Pro
            290                 295                 300

Ala Pro Ala Gly Glu Val Ala Pro Thr Pro Thr Thr Pro Thr Pro Gln
305                 310                 315                 320

Arg Thr Leu Pro Ala
                325

<210> SEQ ID NO 7
<211> LENGTH: 286
<212> TYPE: PRT
<213> ORGANISM: Mycobacterium tuberculosis

<400> SEQUENCE: 7

Asp Pro Glu Pro Ala Pro Pro Val Pro Thr Thr Ala Ala Ser Pro Pro
1               5                   10                  15

Ser Thr Ala Ala Ala Pro Pro Ala Pro Ala Thr Pro Val Ala Pro Pro
                20                  25                  30

Pro Pro Ala Ala Ala Asn Thr Pro Asn Ala Gln Pro Gly Asp Pro Asn
            35                  40                  45

Ala Ala Pro Pro Ala Asp Pro Asn Ala Pro Pro Pro Val Ile
50                  55                  60

Ala Pro Asn Ala Pro Gln Pro Val Arg Ile Asp Asn Pro Val Gly Gly
65                  70                  75                  80

Phe Ser Phe Ala Leu Pro Ala Gly Trp Val Glu Ser Asp Ala Ala His
                85                  90                  95

Phe Asp Tyr Gly Ser Ala Leu Leu Ala Lys Thr Thr Gly Asp Pro Pro
            100                 105                 110

Phe Pro Gly Gln Pro Pro Pro Val Ala Asn Asp Thr Arg Ile Val Leu
        115                 120                 125

Gly Arg Leu Asp Gln Lys Leu Tyr Ala Ser Ala Glu Ala Thr Asp Ser
    130                 135                 140

Lys Ala Ala Ala Arg Leu Gly Ser Asp Met Gly Glu Phe Tyr Met Pro
145                 150                 155                 160

Tyr Pro Gly Thr Arg Ile Asn Gln Glu Thr Val Ser Leu Asp Ala Asn
                165                 170                 175

Gly Val Ser Gly Ser Ala Ser Tyr Tyr Glu Val Lys Phe Ser Asp Pro
            180                 185                 190

Ser Lys Pro Asn Gly Gln Ile Trp Thr Gly Val Ile Gly Ser Pro Ala
        195                 200                 205

Ala Asn Ala Pro Asp Ala Gly Pro Pro Gln Arg Trp Phe Val Val Trp
    210                 215                 220

Leu Gly Thr Ala Asn Asn Pro Val Asp Lys Gly Ala Ala Lys Ala Leu
225                 230                 235                 240

Ala Glu Ser Ile Arg Pro Leu Val Ala Pro Pro Ala Pro Ala Pro
                245                 250                 255

Ala Pro Ala Glu Pro Ala Pro Ala Pro Ala Pro Ala Gly Glu Val Ala
            260                 265                 270

Pro Thr Pro Thr Thr Pro Thr Pro Gln Arg Thr Leu Pro Ala
        275                 280                 285

<210> SEQ ID NO 8
<211> LENGTH: 287
<212> TYPE: PRT
<213> ORGANISM: Mycobacterium leprae -continued

```
<400> SEQUENCE: 8

Met Asn Gln Val Asp Leu Asp Ser Thr His Arg Lys Gly Leu Trp Ala
1               5                   10                  15

Ile Leu Ala Ile Ala Val Val Ala Ser Ala Ser Ala Phe Thr Met Pro
            20                  25                  30

Phe Arg Ala Ala Ala Asn Ala Asp Pro Ala Pro Leu Pro Pro Ser Thr
        35                  40                  45

Ala Thr Ala Ala Pro Ser Pro Ala Gln Glu Ile Ile Thr Pro Leu Pro
    50                  55                  60

Gly Ala Pro Val Ser Ser Glu Ala Gln Pro Gly Asp Pro Asn Ala Pro
65                  70                  75                  80

Ser Leu Asp Pro Asn Ala Pro Tyr Pro Leu Ala Val Asp Pro Asn Ala
                85                  90                  95

Gly Arg Ile Thr Asn Ala Val Gly Gly Phe Ser Phe Val Leu Pro Ala
                100                 105                 110

Gly Trp Val Glu Ser Glu Ala Ser His Leu Asp Tyr Gly Ser Val Leu
            115                 120                 125

Leu Ser Lys Ala Ile Glu Gln Pro Pro Val Leu Gly Gln Pro Thr Val
    130                 135                 140

Val Ala Thr Asp Thr Arg Ile Val Leu Gly Arg Leu Asp Gln Lys Leu
145                 150                 155                 160

Tyr Ala Ser Ala Glu Ala Asp Asn Ile Lys Ala Ala Val Arg Leu Gly
                165                 170                 175

Ser Asp Met Gly Glu Phe Tyr Leu Pro Tyr Pro Gly Thr Arg Ile Asn
            180                 185                 190

Gln Glu Thr Ile Pro Leu His Ala Asn Gly Ile Ala Gly Ser Ala Ser
        195                 200                 205

Tyr Tyr Glu Val Lys Phe Ser Asp Pro Asn Lys Pro Ile Gly Gln Ile
    210                 215                 220

Cys Thr Ser Val Val Gly Ser Pro Ala Ala Ser Thr Pro Asp Val Gly
225                 230                 235                 240

Pro Ser Gln Arg Trp Phe Val Val Trp Leu Gly Thr Ser Asn Asn Pro
                245                 250                 255

Val Asp Lys Gly Ala Ala Lys Glu Leu Ala Glu Ser Ile Arg Ser Glu
            260                 265                 270

Met Ala Pro Ile Pro Ala Ser Val Ser Ala Pro Ala Pro Val Gly
        275                 280                 285
```

METHOD FOR INHIBITING INFLAMMATORY RESPONSES

CONTINUING APPLICATION DATA

This application claims the priority of U.S. Provisional Application Ser. No. 60/121,177, filed Feb. 22, 1999, which is incorporated by reference herein.

GOVERNMENT FUNDING

The present invention was made with government support under Grant No. RO1 HL59324 and RO1 CA44426, awarded by the National Institutes of Health. The Government has certain rights in this invention.

BACKGROUND

Asthma has attracted a great deal of attention from both the public and from the medical community in the past few years. It has been termed an "epidemic," and been the subject of cover stories in major newspapers and magazines. This is primarily due to the observation that the disease is worsening, particularly in Western, industrialized nations. In the past three decades, the prevalence, severity, and mortality of asthma have increased significantly. A recent study estimated the total annual cost in the United States at almost $6 billion. Once thought to be due to airway muscle spasm, asthma is now known to be an inflammatory disorder; during an asthma exacerbation, inflammation precedes bronchospasm. In acute asthma, eosinophils may form up to half of the cellular infiltrate, and bronchoalveolar eosinophilia invariably follows allergen inhalation in asthma attacks. Eosinophils cause inflammation and bronchial hyperreactivity through release of mediators such as leukotrienes, major basic protein, eosinophilic cationic protein, and eosinophilic peroxidase (Bruijnzeel, Ann NY Acad Sci 725, 259–267, (1994)).

Numbers and activity of eosinophils are controlled by cytokines released from activated T cells, especially IL-4, IL-5, and IL-13. T-lymphocytes can be divided on the basis of cytokine production, into Th1 and Th2 (Mosmann, T. R. et al., *J. Immunol.*, 136, 2348–2357, (1986)). Th1 cells produce IL-2 and IFN-γ, but no IL-4 or IL-5, and Th2 cells produce IL-4, IL-5, IL-6, IL-10, and IL-13 but no IL-2 or IFN-γ. Th1 and Th2 cells interact in a counterregulatory fashion: IL-4 and IL-10 promote Th2 development (Parronchi et al., *J. Immunol.*, 149, 2977–2983 (1992), Swain et al., *J. Immunol.*, 145, 3796–3806 (1990)) and inhibit Th1 cell and cytokine production (Moore, K. W. et al., *Science*, 248, 1230–1234 (1990)), and IFN-γ inhibits the proliferation of Th2 cells (Gajewski et al., *J. Immunol.*, 140, 4245–4252 (1988)) and promotes the development of Th1 cells (Parronchi et al., *J. Immunol.*, 149 2977–2983 (1992)). IL-12, mainly a product of activated macrophages, is also a strong promoter of Th1 responses (Bliss, et al., *J. Immunol.*, 156, 887–894 (1996)) and is often considered a Th1 cytokine; many of the activities ascribed to IL-12 are due to induction of IFN-γ. Th1 and Th2 cells have been identified in humans, in vivo as well as in vitro.

The Th2 cytokines, IL-4, IL-5, and IL-13 (Grunig, et al., *Science*, 282, 2261–2263 (1998), Robinson et al., *N. Engl. J. Med.*, 326, 298–304 (1992), Wills-Karp et al., *Science*, 282, 2258–2261 (1998)), have been increasingly implicated in the inflammation of asthma. IL-4 amplifies allergic responses by inducing IgE production by uncommitted B-cells (Del Prete, et al., *J. Immunol.*, 140, 4193–8 (1988)) and is a growth factor for mast cells (Saito, et al., *Proc. Natl. Acad. Sci. USA*, 85, 2288–2292 (1988)). IL-5 also stimulates immunoglobulin secretion (Swain, et al., *J. Immunol.*, 145, 3796–3806 (1990), Takatsu et al., *J. Immunol.*, 124, 2414–2422 (1980)) as well as stimulating the proliferation and activation of eosinophils (Clutterbuck, et al., *Blood* 73, 1504–1512 (1988), Lopez et al., *J. Exp. Med.*, 167, 219–223 (1988), Walsh et al., *Immunol.*, 71, 258–265 (1990)) and basophils (Hirai, K. et al., *J. Exp. Med.*, 172, 1525–1528 (1990)). IL-13 has recently been shown to cause airway hyperresponsiveness and inflammation independently of eosinophils or IL-4 (Grunig et al., *Science*, 282, 2261–2263 (1998), Wills-Karp et al., *Science*, 282, 2258–2261 (1998)). In vitro, allergen-specific T-cell clones from atopic donors release Th2 cytokines after stimulation by specific allergens (Parronchi et al., *Proc. Natl. Acad. Sci. USA*, 88, 4538–4542 (1991)). During asthma exacerbations, peripheral T-cell activation and increased serum IL-5 correlate with eosinophilia and asthma symptoms (Corrigan et al., *Am. Rev. Respir. Dis.*, 147, 540–547 (1993)), and bronchoalveolar lavage (BAL) T-cells release cytokines in a Th2-like pattern (Robinson et al., *J. All. Clin. Immunol.*, 92, 313–324 (1993)), Robinson et al., *N. Engl. J. Med.*, 326, 298–304 (1992), Robinson et al., *J. All. Clin. Immunol.*, 92, 397–403 (1993)). Non-atopic asthmatics also have increased levels of Th2-like cytokines; increased IL-5 release from BAL T-lymphocytes is characteristic of both atopic and non-atopic asthmatics (Walker et al., *Am. Rev. Respir. Dis.*, 146, 109–115 (1992)), and expression of peripheral T-cell IL-5 mRNA from non-atopic asthmatic subjects correlates with increased BAL (Marini et al., *Chest* 102, 661–669 (1992)) and peripheral blood (Walker et al., *Am. Rev. Respir. Dis.*, 146, 109–115 (1992)) eosinophilia.

Because of these observations, the focus of treatment in asthma has shifted from primarily addressing bronchospasm, to one of modulating inflammation. Recent guidelines to the management of asthma recommend that anti-inflammatory therapy be used for all but the most intermittent and benign cases of the disease. Current anti-inflammatory therapy, however, remains disappointingly broad and nonspecific; corticosteroids are the "gold standard" for asthma treatment, and inhaled corticosteroids are only incrementally better than they were 25 years ago. The much-touted leukotriene pathway antagonists which have been released in the last five years have been helpful only in a subset of asthmatics.

SUMMARY OF THE INVENTION

Positive tubercullin skin tests are associated with protection against atopy and asthma (Shirakawa et al., Science, 275, 77≠79 (1997)) as well as systemic Th1 responses; however, the antigen(s) responsible for this protection has not been identified. The Fibronectin Attachment Protein of *Mycobacterium bovis*-BCG (FAP-B) has been identified and cloned. FAP-B is responsible for binding of the organism to fibronectin and for epithelial entry. Other FAPs have been isolated (*M. vaccae* FAP-V) and in some cases cloned (*M. leprae* FAP-L and *M. avium* FAP-A). Functional studies show FAP-B to bind fibronectin via the highly conserved attachment regions previously identified for FAP-A and FAP-L and also to competitively inhibit attachment of BCG to matrix fibronectin.

Surprisingly and unexpectedly, the FAP-B polypeptide is capable of protecting against the induction of an atopic/asthmatic inflammatory response. FAP-B and related polypeptides offer potential therapeutic benefit in asthma. Without intending to be bound by theory, it is expected that the mechanism of action through which FAP-B offers protection against Th2-mediated responses is through induction of Th1 responses, such as IFN-γ and IL-12, which can downregulate Th2 responses.

Accordingly, the present invention provides methods for treating at least one symptom of an inflammatory response in a mammal. In one embodiment, a method includes administering an effective amount of a microbial polypeptide to the mammal such that at least one symptom of an inflammatory response, for instance a Th2 mediated inflammatory response, is inhibited. Optionally, the microbial polypeptide is isolated. The microbial polypeptide can be administered prior to exposure to at least one suspected or known inflammation response-inducing agent, or administered during or after exposure to at least one suspected or known inflammation response-inducing agent.

The microbial polypeptide can be encoded by a nucleotide sequence, where the complement of the nucleotide sequence hybridizes to the nucleotide sequence set forth at nucleotides 79 to 1056 of SEQ ID NO:1 in a solution containing 50% formamide, 6×SSC, 7×Denhardt's reagent, 0.7% SDS, 150 µg/ml salmon sperm DNA at 42° C. for at least about 12 hours, followed by one wash for 30 minutes at 25° C. in a solution containing 1×SSC, one wash for 30 minutes at 42° C. in a solution containing 1×SSC, and one wash for 30 minutes at 42° C. in a solution containing 0.1×SSC. For instance, the nucleotide sequence encoding the microbial polypeptide can be nucleotides 79 to 1056 of SEQ ID NO:1. The microbial polypeptide can also inhibit fibronectin attachment to bacillus Calmette-Guerin in a dose-dependent manner.

The microbial polypeptide can be a Mycobacterial polypeptide. The amino acid sequence of the Mycobacterial polypeptide can be the amino acid sequence of SEQ ID NO:2, GenBank accession AAB34676, GenBank accession AAB50543, GenBank accession CAA56555, GenBank accession AAB36458, GenBank accession P46842, or active analogs and active fragments thereof. Alternatively, the amino acid sequence of the Mycobacterial polypeptide can include amino acids 47 to 325 of SEQ ID NO:2, amino acids 112 to 283 of SEQ ID NO:2, 121 to 283 of SEQ ID NO:2, or active analogs and active fragments thereof. In another alternative, the amino acid sequence of the Mycobacterial polypeptide can be SEQ ID NO:3 and amino acids 47 to 325 of SEQ ID NO:2, and active analogs and active fragments thereof, wherein the carboxy terminal amino acid of SEQ ID NO:3 is fused to the amino terminal amino acid of amino acids 47 to 325 of SEQ ID NO:2.

The inflammatory response can be associated with a disease including skin allergy, hives, allergic rhinitis, conjunctivitis, hay fever, asthma, or allergic gastroenteritis. The types of asthma include extrinsic asthma and intrinsic asthma. When the asthma is extrinsic, it can be allergic asthma, occupational asthma, and allergic bronchopulmonary aspergillosis. When the asthma is intrinsic, it can be associated with an irritant including a pathogen, for instance a pathogen that causes a respiratory tract infection in the mammal, or an inhaled pollutant.

Another aspect of the invention provides a method for treating at least one symptom of an inflammatory response, including asthma, in a mammal including administering to the mammal a polypeptide such that at least one symptom of the inflammatory response is inhibited. The amino acid sequence of the polypeptide is SEQ ID NO:3 and amino acids 47 to 325 of SEQ ID NO:2, and active analogs and active fragments thereof, where the carboxy terminal amino acid of SEQ ID NO:3 is fused to the amino terminal amino acid of amino acids 47 to 325 of SEQ ID NO:2.

The present invention also provides an inflammation reaction inhibiting composition that includes a microbial polypeptide, for instance a Mycobacterial polypeptide, and a pharmaceutically acceptable carrier. In one embodiment, the polypeptide can comprise an amino acid sequence of SEQ ID NO:3 and amino acids 47 to 325 of SEQ ID NO:2, and active analogs and active fragments thereof, where the carboxy terminal amino acid of SEQ ID NO:3 is fused to the amino terminal amino acid of amino acids 47 to 325 of SEQ ID NO:2. In an alternative embodiment, the polypeptide is encoded by a nucleotide sequence, where the complement of the nucleotide sequence hybridizes to the nucleotide sequence set forth at nucleotides 79 to 1056 of SEQ ID NO:1 in a solution containing 50% formamide, 6×SSC, 7×Denhardt's reagent, 0.7% SDS, 150 µg/ml salmon sperm DNA at 42° C. for at least about 12 hours, followed by one wash for 30 minutes at 25° C. in a solution containing 1×SSC, one wash for 30 minutes at 42° C. in a solution containing 1×SSC, and one wash for 30 minutes at 42° C. in a solution containing 0.1×SSC.

The present invention further provides a method for treating symptoms of an inflammatory response in a mammal, including administering an effective amount of a polypeptide to the mammal such that at least one symptom of an inflammatory response is inhibited. The polypeptide is encoded by a nucleotide sequence, where the complement of the nucleotide sequence hybridizes to the nucleotide sequence set forth at nucleotides 79 to 1056 of SEQ ID NO:1 in a solution containing 50% formamide, 6×SSC, 7×Denhardt's reagent, 0.7% SDS, 150 µg/ml salmon sperm DNA at 42° C. for at least about 12 hours, followed by one wash for 30 minutes at 25° C. in a solution containing 1×SSC, one wash for 30 minutes at 42° C. in a solution containing 1×SSC, and one wash for 30 minutes at 42° C. in a solution containing 0.1×SSC.

Definitions

"Treating" refers to the administration of a polypeptide or a composition that includes a polypeptide at any time prior to the onset of at least one symptom of an inflammatory response, i.e., prophylactic therapy. "Treating" also refers to the administration of a polypeptide or a composition that includes a polypeptide during or after the onset of at least one symptom of an inflammatory response to ameliorate at least one symptom of an inflammatory response. In other words, "treating" refers to both the prevention (prophylactic) and to the amelioration (therapeutic) of at least one symptom of an inflammatory response.

Inflammatory response, and symptoms of an inflammatory response are described in greater detail herein. An inflammatory response-inducing agent is a substance that induces an inflammatory response in a mammal. Non-limiting examples of inflammatory response-inducing agents include allergens, particulates, pathogens, and pollutants such as tobacco smoke. "Exposure" to inflammatory response-inducing agents indicates that a mammal is in an environment where inflammatory response-inducing agents are present or may be present.

An "effective amount" of a polypeptide refers to an amount of the polypeptide that is sufficient to inhibit in a mammal at least one symptom of an inflammatory response.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

A polypeptide can be produced by an organism, or produced using recombinant techniques, or chemically or enzymatically synthesized. A "microbial polypeptide" refers to a polypeptide that is expressed by a microbe, is encoded by a coding region isolated from a microbe, is encoded by a coding region that hybridizes with a nucleotide sequence as described in greater detail herein or that has a certain percentage structural similarity with a nucleotide sequence as described in greater detail herein, or has a certain percentage structural similarity with a polypeptide as described herein. A type of microbial polypeptide is "mycobacterial polypeptide," where "mycobacterial" refers to a strain of the genus Mycobacterium. A coding region refers to a polynucleotide that encodes a polypeptide, usually via mRNA, when placed under the control of appropriate regulatory sequences. The boundaries of the coding region are generally determined by a translation start codon at its 5' end and a translation stop codon at its 3' end.

An active analog or active fragment of a polypeptide is one that retains the ability to treat the symptoms of an inflammatory response in an animal as described herein. Active analogs and active fragments are described in greater detail herein.

The term "complement" and "complementary" as used herein, refers to the ability of two single stranded polynucleotides to base pair with each other, where an adenine on one polynucleotide will base pair to a thymine on a second polynucleotide and a cytosine on one polynucleotide will base pair to a guanine on a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The terms complement and complementary also encompass two polynucleotides where one polynucleotide contains at least one nucleotide that will not base pair to at least one nucleotide present on a second polynucleotide. For instance the third nucleotide of each of the two polynucleotides 5'-ATTGC and 5'-GCTAT will not base pair, but these two polynucleotides are complementary as defined herein. Typically two polynucleotides are complementary if they hybridize under certain conditions.

As used herein, "hybridizes," "hybridizing," and "hybridization" means that a single stranded polynucleotide forms a noncovalent interaction with a complementary polynucleotide under certain conditions, as described herein.

Unless noted otherwise, a "pathogen" as used herein refers to a virus or a microbe, including prokaryotic microbes and eukaryotic microbes, that is capable of causing a respiratory tract infection in a mammal, whether the mammal is immunocompromised or not. The terms "bacillus Calmette-Guerin" and *M. bovis* BCG are used interchangeably and refer to a strain of *M. bovis* that has been rendered completely avirulent.

An "isolated" polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities.

BRIEF DESCRIPTION OF THE FIGURES

FIG. 1. Nucleotide sequence (SEQ ID NO:1) and amino acid sequence (SEQ ID NO:2) of FAP-B. The signal sequence is underlined; the first 17 amino acids (amino acids 40–56 of SEQ ID NO:2) corresponding to BCG 45/47 kDa antigen are in bold.

DETAILED DESCRIPTION OF THE INVENTION

Figure 2:
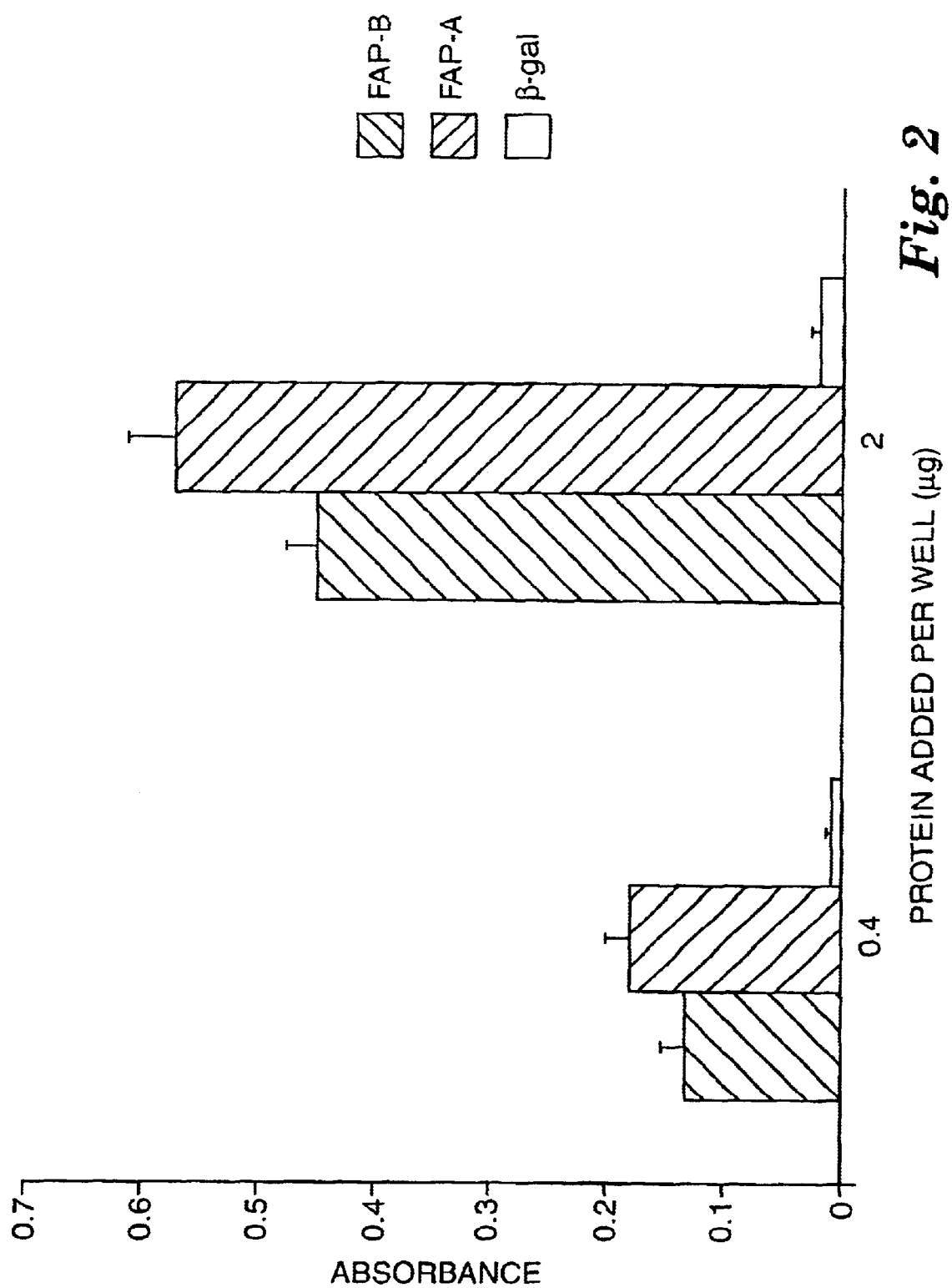
FIG. 2. Binding of purified FAP-B, FAP-A, and control recombinant β-galactosidase (β-gal) to fibronectin.

The present invention provides methods for inhibiting at least one symptom of an inflammatory response in a mammal, preferably a mouse or a human, most preferably a human. The methods include administering an effective amount of a polypeptide, preferably a microbial polypeptide, more preferably a Mycobacterial polypeptide, to a mammal. The polypeptides that can be used in the methods are described in greater detail herein. The administration causes the inhibition of at least one symptom of an inflammatory response in the mammal. Preferably, the at least one symptom is the result of an inflammatory response in which Th2 cells release cytokines, including for example, IL4, IL-5, IL-8, and IL-13, that regulate the inflammatory response. Such an inflammatory response is referred to herein as a Th2 mediated inflammatory response.

Examples of symptoms of an inflammatory response, preferably a Th2 mediated inflammatory response, include, for instance, those associated with skin allergy, hives, allergic rhinitis, conjunctivitis, eczema, hay fever, asthma, or allergic gastroenteritis, pulmonary eosinophilia, eosinophilic-myalgia syndrome, tropical eosinophilia, hypereosinophilic syndrome, and Churg-Strauss syndrome, and parasitic infections, including schistosomiasis, preferably asthma. Other symptoms of an inflammatory response can include pain, swelling, redness, warmth, and itching.

The types of asthma include extrinsic asthma (e.g., asthma initiated by an inhaled antigen) and intrinsic asthma (e.g., asthma initiated by non-immune mechanisms), for example. Types of extrinsic asthma include, for instance, allergic asthma, occupational asthma, and allergic bronchopulmonary aspergillosis. Extrinsic asthma is typically associated with a specific immune response to an antigen (e.g., IgE interacting with an antigen). Intrinsic asthma includes asthma associated with an irritant, for instance, a pathogen, preferably a pathogen that can or has caused a respiratory tract infection in the mammal. Non-limiting examples of pathogens that have been associated with the development and/or progression of asthma include respiratory syncytial virus, coronavirus, parainfluenza virus, and rhinovirus. Other irritants associated with intrinsic asthma include, for instance, inhaled pollutants such as respirable particulates, environmental tobacco smoke, ozone, $SO_2$, and $NO_2$.

Symptoms of asthma include airway inflammation, which typically causes other symptoms including airway hyperresponsiveness and airflow limitation (National Asthma Education and Prevention Program, Expert Panel Report 2: Guidelines for the Diagnosis and Management of Asthma, Bethesda, Md., National Institutes of Health, pp. 7–13, (1997)). Measurement of the symptoms of asthma includes evaluating the presence of denudation of airway epithelium, collagen deposition beneath basement membrane, edema, mast cell activation, inflammatory cell infiltration including neutrophils, eosinophils, and lymphocytes, and the presence of cytokines associated with Th2 cells including IL-4, IL-5, IL-9, and IL-13. Preferably, eosinophil infiltration is measured. Methods known to the art can be used to access the airway and measure symptoms associated with asthma, including, for instance, fiberoptic bronchoscopy, lavage, or biopsy (Beasley et al., *Am. Rev. Respir. Dis.,* 139, 806–817 (1989), Jeffery et al., *Am. Rev. Respir. Dis.,* 140, 1745–1753 (1989), and Laitinen et al., *Am. Rev. Respir. Dis.,* 131, 599–606 (1985)). Measurement of airway hyperresponsiveness includes inhalation challenge testing with methacholine, or histamine (O'Connor et al., *Am. Rev. Respir. Dis.,* 140, 225–252 (1989)). Airway hyperresponsiveness can also be measured after hyperventilation with cold dry air, inhalation of hypotonic or hypertonic aerosols, or after exercise (O'Connor et al., *Am. Rev. Respir. Dis.,* 140, 225–252 (1989)). Variability between morning and evening peak expiratory flow may also be used as a measure of airway hyperresponsiveness.

The present invention further provides a pharmaceutical composition that includes a polypeptide, preferably a microbial polypeptide, more preferably a Mycobacterial polypeptide, that is useful in the methods of the present invention, and a pharmaceutically acceptable carrier. The compositions of the present invention are formulated in pharmaceutical preparations in a variety of forms adapted to the chosen route of administration. Formulations include those suitable for parenteral administration or for perfusion.

The formulations may be conveniently presented in unit dosage form and may be prepared by methods well known in the art of pharmacy. Typically, methods of preparing a pharmaceutical composition include the step of bringing the active compound (e.g., a polypeptide useful in the methods of the present invention) into association with a carrier which constitutes one or more accessory ingredients. In general, the formulations are prepared by uniformly and intimately bringing the active compound into association with a liquid carrier, a finely divided solid carrier, or both, and then, if necessary, shaping the product into the desired formulations.

The polypeptides of the invention can be incorporated directly into the food of a mammal's diet, as an additive, supplement, or the like. Thus, the invention further provides a food product containing a polypeptide of the invention. Any food is suitable for this purpose, although processed foods already in use as sources of nutritional supplementation or fortification, such as breads, cereals, milk, and the like, may be more convenient to use for this purpose.

Formulations suitable for parenteral administration conveniently comprise a sterile aqueous preparation of the composition, or dispersions of sterile powders that include the composition, which are preferably isotonic with the blood of the recipient. Isotonic agents that can be included in the liquid preparation include sugars, buffers, and sodium chloride. Solutions of the composition can be prepared in water, optionally mixed with a nontoxic surfactant. Dispersions of the composition can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the composition, preferably by filter sterilization. Preferred methods for preparing powders include vacuum drying and freeze drying of the sterile injectable solutions. Subsequent microbial contamination can be prevented using various antimicrobial agents, for example, antibacterial, antiviral, and antifungal agents including parabens, chlorobutanol, phenol, sorbic acid, thimerosal, and the like. Absorption of the composition by the mammal over a prolonged period can be achieved by including agents for delaying, for example, aluminum monostearate and gelatin.

In addition to the aforementioned ingredients, the formulations of this invention may further include one or more accessory ingredients including diluents, buffers, binders, disintegrants, surface active agents, thickeners, lubricants, preservatives (including antioxidants), and the like.

The formulations include those suitable for parenternal administration including subcutaneous, intramuscular, intraperitoneal, intravenous, and aerosol administration. Preferably, the composition of the invention is administered intravenously, or by aerosol. Aerosols can be delivered by, for instance, oral and/or nasal inhalation from a metered dose inhaler. Useful dosages of the compositions can be determined by comparing their in vitro activity and the in vivo activity in animal models. Methods for extrapolation of effective dosages in mice, and other mammals, to humans are known in the art; for example, see Borch et al. (U.S. Pat. No. 4,938,949).

Polypeptides and Polynucleotides

A polypeptide of the present invention is typically capable of inhibiting at least one symptom of an inflammatory response in a mammal, preferably a Th2 mediated response. Optionally, a polypeptide of the invention is also able to specifically inhibit attachment of fibronectin to bacillus Calmette-Guerin. The ability to inhibit at least one symptom of an inflammatory response, and the specific inhibition of fibronectin attachment to bacillus Calmette-Guerin, can be measured as described herein. A polypeptide can be present in, for instance, a cell lysate, or the polypeptide can be isolated or purified. Preferably, the polypeptide is isolated, more preferably, purified.

The polypeptides useful in some aspects of the invention are produced by a prokaryotic microbe, and more preferably a strain of the genus Mycobacterium, including, for instance, M. leprae, M. vaccae, M. tuberculosis, M. avium, M smegmatis, M. kansasii, M. bovis, and M. bovis BCG. Preferably, the Mycobacterial polypeptide is produced by M. bovis BCG. Examples of Mycobacterial polypeptides useful in the methods of the present invention include the Fibronectin Attachment Proteins (FAPs), including FAP-L

1 MNQVDLDSTH RKGLWAILAI AVVASASAFT MPLPAAANAD PAPLPPSTAT AAPSPAQEII
61 TPLPGAPVSS EAQPGDPNAP SLDPNAPYPL AVDPNAGRIT NAVGGFSFVL PAGWVESEAS
121 HLDYGSVLLS KAIEQP PVLG QPTVVATDTR IVLGRLDQKL YASAEADNIK AAVRLGSDMG
181 EFYLPYPGTR INQETIPLHA NGIAGSASYY EVKFSDPNKP IGQICTSVVG SPAASTPDVG
241 PSQRWFVVWL GTSNNPVDKG AAKELAESIR SEMAPIPASV SAPAPVG (which is produced by *M. leprae* and depicted at SEQ ID NO:4, and GenBank accession No. AAB34676), FAP-A 1 MDQVEATSTR RKGLWTTLAI TTVSGASAVV IALPETSHAD PEVPTPVPPS TATTPHPRRR
61 RIPGQPADNA QAGAPAPAPN GQQRPPRRRR MIPTRAPPPA GAPPNGAPPA APNGAPPPPV
121 DPNAPPPPPA DPNAGRIPNS YVLPAGWVES DASHLDYGSA LLSKVTGPPP MPDQPPPVAN
181 DTRIVMGRVD QKLYASAEAN NAKAAVGLGS DMGEFFMPYP GTRINQDSTP LNGANGSTGS
241 ASYYEVKFSD ASKPNGQIWT GVIGSANAGN RQRWFVVWLG TSNDPVDKVA AKALAESIQA
301 WTPPPAPPAA PGGPGAPAPG APGAPAPGAP AAPGVTAPAA PAPAAPGAPA APGAPAPEPG
361 QAPAVEVSPT PTPTPQQTLS A (which is produced by *M. avium* and depicted at SEQ ID NO:5, and GenBank accession No. AAB50543), and FAP-B (which is produced by *M. bovis* BCG and depicted at SEQ ID NO:2, and GenBank accession No. AAB71842). Other examples of Mycobacterial polypeptides useful in the methods of the present invention include the *M. tuberculosis* 45/47 protein 1 MHQVDPNLTR RKGRLAALAI AAMASASLVT VAVPATANAD PEPAPPVPTT AASPPSTAAA
61 PPAPATPVAP PPPAAANTPN AQPGDPNAAP PPADPNAPPP PVIAPNAPQP VRIDNPVGGF
121 SFALPAGWVE SDAAHFDYGS ALLSKTTGDP PFPGQPPPVA NDTRIVLGRL DQKLYASAEA
181 TDSKAAARLG SDMGEFYMPY PGTRINQETV SLDANGVSGS ASYYEVKFSD PSKPNGQIWT
241 GVIGSPAANA PDAGPPQRWF VVWLGTANNP VDKGAAKALA ESIRPLVAPP PAPAPAPAEP
301 APAPAPAGEV APTPTTPTPQ RTLPA (depicted at SEQ ID NO:6, and GenBank accession No. CAA56555), the *M. tuberculosis* 45 kDa culture filtrate glycoprotein 1 DPEPAPPVPT TAASPPSTAA APPAPATPVA PPPPAAANTP NAQPGDPNAA PPPADPNAPP
61 PPVIAPNAPQ PVRIDNPVGG FSFALPAGWV ESDAAHFDYG SALLAKTTGD PPFPGQPPPV
121 ANDTRIVLGR LDQKLYASAE ATDSKAAARL GSDMGEFYMP YPGTRINQET VSLDANGVSG
181 SASYYEVKFS DPSKPNGQIW TGVIGSPAAN APDAGPPQRW FVVWLGTANN PVDKGAAKAL
241 AESIRPLVAP PPAPAPAPAE PAPAPAPAGE VAPTPTTPTP QRTLPA (depicted at SEQ ID NO:7, and GenBank accession No. AAB36458), and the *M. leprae* antigen 43L precursor 1 MNQVDLDSTH RKGLWAILAI AVVASASAFT MPFRAAANAD PAPLPPSTAT AAPSPAQEII
61 TPLPGAPVSS EAQPGDPNAP SLDPNAPYPL AVDPNAGRIT NAVGGFSFVL PAGWVESEAS
121 HLDYGSVLLS KAIEQPPVLG QPTVVATDTR IVLGRLDQKL YASAEADNIK AAVRLGSDMG
181 EFYLPYPGTR INQETIPLHA NGIAGSASYY EVKFSDPNKP IGQICTSVVG SPAASTPDVG
241 PSQRWFVVWL GTSNNPVDKG AAKELAESIR SEMAPIPASV SAPAPVG (depicted at SEQ ID NO:8, and GenBank No. accession P46842). Preferably, the Mycobacterial polypeptide is FAP-B (SEQ ID NO:2), more preferably amino acids 40–325 of SEQ ID NO:2, most preferably amino acids 47–325 of SEQ ID NO:2. Alternatively, the Mycobacterial polypeptide has the amino-terminal domain of amino acid sequence SEQ ID NO:3 (which is described herein) fused to amino acids 47 to 325 of SEQ ID NO:2.

Polypeptides useful in some aspects of the invention include those having a significant level of similarity with the amino acid sequence of SEQ ID NO:2, more preferably amino acids 40–325 of SEQ ID NO:2, most preferably amino acids 47–325 of SEQ ID NO:2. The similarity is referred to as structural similarity and is generally determined by aligning the residues of the two amino acid sequences (i.e., a candidate amino acid sequence and the amino acid sequence of SEQ ID NO:2) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in the amino acid sequence of SEQ ID NO:2. A candidate amino acid sequence can be isolated from an organism, preferably a microbe, or can be artificially constructed by using, for instance, recombinant techniques, or chemically or enzymatically synthesized. Preferably, two amino acid sequences are compared using the Blastp program, version 2.0.9, of the BLAST 2 search algorithm, as described by Tatusova, et al. (*FEMS Microbiol Lett* 1999, 174:247–250), and available at www.ncbi.nlm.nih.gov/gorf/b12.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identities." Preferably, a polypeptide includes an amino acid sequence having a structural similarity with the amino acid sequence of SEQ ID NO:2 of, in increasing order of preference, greater than 61% identity, at least about 70% identity, at least about 80% identity, most preferably at least about 90% identity.

Alternatively, a polypeptide useful in some aspects of the invention is encoded by a polynucleotide, the complement of which hybridizes to nucleotides 79 to 1056 of SEQ ID NO:1 under standard hybridization conditions as defined herein. Polynucleotides encoding polypeptides useful in some aspects of the invention also include those having a significant level of similarity with nucleotides 79 to 1056 of SEQ ID NO:1, i.e., the coding region present in SEQ ID NO:1. The similarity is referred to as structural similarity and is determined by aligning the residues of the two polynucleotides (i.e., the nucleotide sequence of the candidate nucleotide sequence and the nucleotides 79 to 1056 of SEQ ID NO:1) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate nucleotide sequence is the sequence being compared to nucleotides 79 to 1056 of SEQ ID NO:1. Preferably, two nucleotide sequences are compared using the Blastn program, version 2.0.9, of the BLAST 2 search algorithm, as described by Tatusova, et al. (*FEMS Microbiol Lett* 1999, 174:247–250), and available at www.ncbi.nlm.nih.gov/gorf/b12.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, a polynucleotide includes a nucleotide sequence having a structural similarity with nucleotides 79 to 1056 of SEQ ID NO:1 of, in increasing order of preference, greater than 61% identity, at least about 70% identity, at least about 80% identity, most preferably at least about 90% identity.

Optionally, individual organisms, preferably microbes, can be screened for the presence of polypeptides that specifically inhibit attachment of fibronectin to bacillus Calmette-Guerin. Typically, such polypeptides are isolated from a microbe as described in Example 1, and evaluated for the ability to specifically inhibit attachment of fibronectin to bacillus Calmette-Guerin as described in Example 5. Polypeptides identified in this way can be evaluated using the mammal model described in Example 6. Once a polypeptide is identified that decreases eosinophilia or decreases responsiveness to inhaled methacholine, the polypeptide can be used in the methods of the present invention, or the polynucleotide sequence encoding the polypeptide can be isolated using methods detailed herein.

The polypeptides useful in some aspects of the invention include an active analog and active fragment of SEQ ID NO:2, or GenBank accession Nos. AAB34676, AAB50543, CAA56555, AAB36458, or P46842. An active analog or active fragment of a polypeptide is one that is expressed by a microbe and is able to inhibit at least one symptom of an inflammatory response in a mammal, and optionally specifically inhibit attachment of fibronectin to bacillus Calmette-Guerin. Active analogs of a polypeptide include polypeptides having amino acid substitutions that do not eliminate the ability to inhibit at least one symptom of an inflammatory response in a mammal, and optionally specifically inhibit attachment of fibronectin to bacillus Calmette-Guerin. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Active analogs, as that term is used herein, also include modified polypeptides. Modifications of polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

Active fragments of a polypeptide include a portion of the polypeptide containing deletions or additions of one or more contiguous or noncontiguous amino acids such that the resulting polypeptide will inhibit at least one symptom of an inflammatory response in a mammal, and optionally specifically inhibit attachment of fibronectin to bacillus Calmette-Guerin. A preferred example of an active fragment of SEQ ID NO:2 are amino acids 112 to 283, more preferably amino acids 121 to 283.

Alternatively, a polypeptide useful in some aspects of the invention is encoded by a polynucleotide, the complement of which hybridizes to nucleotides 79 to 1056 of SEQ ID NO:1 under standard hybridization conditions as defined herein. Polynucleotides encoding polypeptides useful in some aspects of the invention also include those having a significant level of similarity with nucleotides 79 to 1056 of SEQ ID NO:1, i.e., the coding region present in SEQ ID NO:1. The similarity is referred to as structural similarity and is determined by aligning the residues of the two polynucleotides (i.e., the nucleotide sequence of the candidate nucleotide sequence and the nucleotides 79 to 1056 of SEQ ID NO:1) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate nucleotide sequence is the sequence being compared to nucleotides 79 to 1056 of SEQ ID NO:1. Preferably, two nucleotide sequences are compared using the Blastn program, version 2.0.9, of the BLAST 2 search algorithm, as described by Tatusova et al. (*FEMS Microbiol Lett* 1999, 174:247–250), and available at http://www.ncbi.nlim.nih.gov/gorf/b12.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, a polynucleotide includes a nucleotide sequence having a structural similarity with nucleotides 79 to 1056 of SEQ ID NO:1 of, in increasing order of preference, greater than 61% identity, at least about 70% identity, at least about 80% identity, most preferably at least about 90% identity.

Individual organisms, preferably microbes, can be screened for the presence of nucleotide sequences that are similar to nucleotides 79 to 1056 of SEQ ID NO:1. Screening methods include, for instance, hybridization of polynucleotides immobilized on a membrane with a detectably labeled probe. Standard hybridizing conditions use hybridization buffer containing 50% formamide, 6×SSC, 5× to 10×Denhardt's reagent, 0.5% to 1.0% SDS, 100 μg/ml to 200 μg/ml salmon sperm DNA containing labeled probe (1×SSC: 0.15 M NaCl, 0.015 M sodium citrate; 50×Denhardt's reagent: 1% Ficoll Type 400, 1% polyvinylpyrrolidone, and 1% bovine serum albumin Fraction V). referably, the hybridization buffer contains 50% formamide, 6×SSC, 7×Denhardt's reagent, 0.7% SDS, 150 μg/ml salmon sperm DNA and labeled probe. Hybridization is allowed to occur at 42° C. for at least about 12 hours. The membrane is washed once for 30 minutes at 25° C. in a solution containing 1×SSC, once for 30 minutes at 42° C. in a solution containing 1×SSC, and once for 30 minutes at 42° C. in a solution containing 0.1×SSC. Generally the probe does not have to be complementary to all the nucleotides of a polynucleotide as long as there is hybridization under the conditions described herein.

Preferred probes for identifying polynucleotides encoding a polypeptide that inhibits at least one symptom of an inflammatory response in a mammal, and optionally specifically inhibits attachment of fibronectin to bacillus Calmette-Guerin are polynucleotides complementary to a portion of nucleotides 79 to 1056 of SEQ ID NO:1. A probe is typically no greater than about 975 bases and no less than about 10 bases. Methods of detectably labeling a probe are known to the art. The polynucleotide that is identified by the probe is further analyzed using methods known to one of ordinary skill in the art to determine if it encodes a polypeptide that inhibits at least one symptom of an inflammatory response in a mammal, and optionally specifically inhibits attachment of fibronectin to bacillus Calmette-Guerin. Another method for screening individual microorganisms for the presence of nucleotide sequences that are similar to a portion of nucleotides 79 to 1056 of SEQ ID NO:1 is the polymerase chain reaction (PCR). Primer pairs can be designed using methods known to the art that will amplify a portion of nucleotides 79 to 1056 of SEQ ID NO:1. Such a primer pair can be used to screen individual microorganisms for the presence of nucleotide sequences that are similar to nucleotides 79 to 1056 of SEQ ID NO:1.

A polynucleotide encoding a polypeptide useful in the methods of the present invention can be inserted in a vector. Construction of vectors containing a polynucleotide of the invention employs standard ligation techniques known in the art. See, e.g., Sambrook et al, *Molecular Cloning: A Laboratory Manual.,* Cold Spring Harbor Laboratory Press (1989) or Ausubel, R. M., ed. *Current Protocols in Molecular Biology* (1994). A vector can provide for further cloning (amplification of the polynucleotide), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Typically, a vector is capable of replication in a bacterial host, for instance *E. coli.* Preferably the vector is a plasmid. A vector containing a polynucleotide encoding a polypeptide useful in the methods of the present invention can be introduced to a microbe using methods known to the art. The appropriate method to use varies depending on the type of microbe, and include, for instance, $CaCl_2$ mediated transformation, electroporation, and transduction.

An expression vector optionally includes regulatory regions operably linked to the coding region. The invention is not limited by the use of any particular promoter, and a wide variety are known. Promoters act as regulatory signals that bind RNA polymerase in a cell to initiate transcription of a downstream (3' direction) coding region. The promoter used in the invention can be a constitutive or an inducible promoter. It can be, but need not be, heterologous with respect to the host cell. Typically, a promoter results in greater expression of the operably linked coding region when compared to expression of the coding region when operably linked to its natural promoter. Preferred promoters for bacterial transformation include lac, lacUV5, tac, trc, T7, SP6 and ara.

An expression vector can optionally include a Shine Dalgarno site (e.g., a ribosome binding site), and a start site (e.g., the codon ATG) to initiate translation of the transcribed message to produce the enzyme. It can also include a termination sequence to end translation. The polynucleotide used to transform the host cell can optionally further include a transcription termination sequence. The rrnB terminators, which is a stretch of DNA that contains two terminators, T1 and T2, is an often used terminator that is incorporated into bacterial expression systems (J. Brosius et al., (1981) *J. Mol. Biol.* 148 107–127).

A polynucleotide encoding a polypeptide useful in the invention can be altered by inserting a series of nucleotides in frame with the coding region, such that the resulting fusion polypeptide contains a polypeptide useful in the invention fused to an additional domain. This can be used to introduce domains that can facilitate the isolation of the polypeptide. For instance, domains useful in the isolation of a fusion polypeptide that contains a polypeptide useful in the invention include, for example, a histidine domain (which can be isolated using nickel-chelating resins), or an S-peptide domain (which can be isolated using an S-protein, see Kim, J.-S. et al. *Protein Sci.,* 2, 348–356 (1993)). Domains useful in targeting a polypeptide to the exterior surface of a cell, for instance a signal peptide, can also be introduced.

Optionally, the vector includes one or more marker sequences, which typically encode a polypeptide that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, and tetracycline.

The present invention is illustrated by the following examples. It is to be understood that the particular examples, materials, amounts, and procedures are to be interpreted broadly in accordance with the scope and spirit of the invention as set forth herein, and are not intended to limit the invention in any way.

EXAMPLE 1

Isolation of a Fibronectin Attachment Protein (FAP) from Mycobacterium

A FAP polypeptide was isolated from *M. vaccae* and from *M. bovis* BCG as described in U.S. Pat. No. 5,618,916

(Ratliff et al.). The FAP polypeptides are referred to as p55 in this example.

Chemicals

All chemicals were purchased from Sigma (St. Louis, Mo.) and were reagent grade unless otherwise stated.

Bacteria

BCG were obtained from Armand Frappier, Quebec, Canada, as a lyophilized preparation containing 10.sup.7 colony forming units (CFU) mg$^{-1}$ manufacturer's specification). Before use, BCG was cultured in Youman's medium or 5 d at 37° C. The bacteria were harvested by centrifugation and resuspended in buffer to produce approximately 7×10$^8$ CFU ml$^{-1}$ (determined by standard curves plotting $OD_{570}$ vs CFU). $M.$ $vaccae$ was obtained from the mycobacterial culture collection of Dr. John Stanford, University of London, London, England. $M.$ $vaccae$ was grown in Sauton medium and stored at −70° C. as described. Sher et al., ($Infect$ $and$ $Immun.$, 8, 736–742 (1973)).

Preparation of $^{125}$I-labelled Fibronectin (FN)

Human plasma FN was purified as previously described (Kavoussi et al., $J.$ $Clin.$ $Invest.$, 85, 62–67 (1990)). The purified FN, 1.5 mg ml$^{-1}$ was labelled for 15 minutes with 1 mCi (37 MBq) $^{125}$INa (Amersham) in a test-tube precoated with 200 μg Iodo-Gen (1,3,4,6-tetrachloro-3, 6-diphenylglycouril) as previously described. (Aslanzadeh et al., $J.$ $Gen.$ $Microbiol.$, 135, 2735–2741 (1989)). The labelled FN was then separated from unbound $^{125}$I by chromatography on a 10 ml Sephadex G25 column. The specific activities of the labelled FN preparations were routinely between 10$^6$ and 10$^7$cpm μg$^{-1}$.

$^{125}$I-FN Binding Assay

The binding assay was performed as previously described. (Aslanzadeh et al., $J.$ $Gen.$ $Microbiol.$, 135, 2735–2741 (1989)). Briefly, six micrograms of $^{125}$I-FN was added to 1.5 ml volume microcentrifuge tubes (Eppendorf) precoated for 2 hours with 1 ml of 1 mg/ml human serum albumin (HSA). Prior to $^{125}$I-FN addition, 7×10$^6$ BCG suspended in 1.0 ml of 0.1M-Tris buffer, pH 6.0, was added. The $^{125}$I-FN was mixed with either 300 μl unlabelled FN (1 mg/ml) or 300 μl of TRIS only to determine non-specific and total binding, respectively. Specific binding was ascertained by subtracting non-specific from total binding. The reaction mixtures were incubated for 1 hour at 22° C. After incubation, the microcentrifuge tubes containing the reaction mixtures were centrifuged at 10,000 g for 3 minutes in a Beckman Microcentrifuge B. The supernatant, containing free radiolabelled FN, was carefully removed. The microcentrifuge tubes were sliced and the pellets containing the radiolabelled FN bound to BCG were analyzed for radioactivity. Control experiments using $^{125}$I-FN without bacteria produced background counts of approximately 500 cpm.

Attachment of BCG to FN-coated Surfaces

The matrix attachment assay was performed by a modification of a previously described method. Ratliff et al., ($J.$ $Gen.$ $Microbiol.$, 134, 1307–1313 (1988)) Briefly, a 5 day culture was washed twice with and resuspended in phosphate-buffered saline (PBS), pH 7.2, to a concentration of 10$^8$ CFU/ml. 10$^7$ CFU (0.1 ml) was added to each well of a 96 well microtiter plate (Immulon II, Dynatech Laboratories, Inc., Chantilly, Va.) previously coated with (120 μg/ml) of FN or HSA (120 μg/ml; background). Attachment was quantitated by reading the optical density at 570 nm on an ELISA reader.

Production of Receptor-Containing Supernatants $M.$ $vaccae$ were subcultured in 100 ml of Sautons medium to plateau growth phase. An innoculum of 8×10$^8$ bacteria were cultured in each of eight flasks containing 1.0 L of Sautons. Cultures were maintained at 37° C. in 7% $CO_2$ for 3 weeks. Supernatants were harvested by centrifugation and residual bacteria were removed by filtration (2 micron filters, Costar). The supernatant was concentrated 100 times on an Amicon filtration unit with a PM 10 filter. Concentrated $M.$ $vaccae$ culture supernatant was dialyzed against distilled $H_2O$ and lyophilized.

Purification of the FN-Binding Protein

Concentrated $M.$ $vaccae$ culture supernatant was dialyzed against distilled $H_2O$ and lyophilized. The lyophilized supernatant was reconstituted to 1.5 ml with 0.02M Bis-Tris, pH 6.0., and 0.7 ml was loaded onto an ACA 54 gel filtration column (0.6 cm×75 cm) equilibrated with 0.02M Bis-Tris. Inhibitory fractions were pooled and loaded onto 10 ml of DEAE-Sephacel. The column was washed with 0.02M Bis-Tris, pH 6.0 until the effluent was protein free. Protein was eluted with a 0–0.4M NaCl gradient in Bis-Tris. Fractions, 1.0 ml, were collected and dialyzed against Bis-Tris, pH 6.0. SDS-PAGE and Western blots were performed as described (Abou-Zeid et al., $Infect$ $Immun.$, 56, 3046–3051 (1988)).

Antibodies

Polyclonal rabbit antibodies to the purified adhesin (p55) was prepared by injecting subcutaneously 25 μg in alum. At 3 week intervals the rabbit was boosted with 15–20 μg in alum. Ten to 14 days after the second boost antibody was harvested. IgG was isolated from serum by 50% ammonium sulfate precipitation followed by DEAE-Sephacel ion exchange chromatography. SDS-PAGE demonstrated only bands consistent with IgG heavy and light chains. All experiments using the polyclonal antibody were performed with DEAE purified antibody.

Monoclonal antibody to the p55 protein was generated by the subcutaneous injection of BALB/C mice with 10 μg p55 in alum. Mice were boosted three times at weekly intervals with 5 μg p55 in alum. Mice were rested 3–4 weeks after the third boost and injected IV with 5 μg p55 in PBS. Three days later spleens were harvested and fused with the NS1 myeloma. Reactive clones were detected by ELISA with purified p55-coated microtiter wells. A single hybridoma showed consistent reactivity in an ELISA assay. The reactive hybridoma was clones, and the antibody, designated mFNR.1, isotyped as IgMλ.

p55 FN binding Assay

Immulon wells were coated with FN or BSA as a control for non-specific binding, as described above. The remaining attachment sites were blocked by the addition of 1% bovine serum albumin (BSA) in PBS for 30 minutes. Purified p55 in Tris buffer was added to appropriate wells (3 μg/well) and incubated for 30 min at room temperature. Wells were washed and purified mFNR.1 diluted in PBS containing 0.1% BSA was added for 1 hr at room temperature. The wells were washed and a biotinylated anti-mouse IJ (Sigma Chemicals, St. Louis, Mo.) was added at a predetermined optimal concentration for 1 hr. at room temperature. The wells were washed, and the reaction was developed by the addition of p-Nitrophenyl phosphate. Reactivity was read on an ELISA reader at a wave length of 405 nm. Controls included p55 added BSA-coated wells, FN-coated wells without p55, and FN-coated wells with a nonspecific primary isotype control (RL172.4; anti-thy 1.2). Control absorbance for all controls was equal to or less than that of the isotype control.

Results

Concentrated $M.$ $vaccae$ supernatant contains a component that inhibits FN binding to BCG. Purification of the inhibitory component(s) was initiated by applying supernatant to an ACA-54 gel filtration column previously equilibrated with Bis-Tris, pH 6.0. The inhibitory activity was localized and pooled for further purification. SDS-PAGE on the pooled fractions revealed a primary protein band at 55 kDa (p55). The pooled ACA-54 inhibitory fractions were applied to a DEAE-Sephacel anion exchange column equilibrated with 0.02M Bis-Tris, pH 6.0. Bound protein was eluted with a 0–0.4M NaCl gradient in Bis-Tris, pH 6.0. The peak inhibitory activity eluted at 0.3M NaCl. SDA-PAGE on the 0.3M fraction revealed a single 55 kDa protein band. The protein from this fraction was used for all subsequent experiments and for immunization purposes. The protein purification scheme is summarized in Table 1. Amino acid sequencing by Edman degradation was unsuccessful, presumably because the amino terminus of p55 was blocked.

TABLE 1

Purification of p55

| Step | Protein (mg/ml) | Volume | Total Protein | Fold Purification |
|---|---|---|---|---|
| Conc. Supernatant | 11.16 | 0.7 | 7.8 | — |
| ACA 54 Gel Filtration | 0.07 | 8.0 | 0.57 | 13.7 |
| DEAE-Sephacel (0–0.4 NaCl) | 0.16 | 2.0 | 0.32 | 24.3 |

The purified p55 was tested for its ability to inhibit $^{125}$I-FN binding to BCG; purified p55 inhibited FN attachment to BCG in a dose-dependent manner.

Purified p55 was used as an immunogen to generate a rabbit polyclonal and a mouse monoclonal antibody. The resulting polyclonal antibody blotted a single protein band at 55 kDa in crude M. vaccae supernatants. The single monoclonal antibody obtained was reactive by ELISA to purified p55 but was not effective in Western blots.

Further studies were performed to determine whether the purified p55 protein bound to FN. Microtiter wells were coated with FN as described above, after which purified p55 was added. The binding of p55 to FN was detected by either the polyclonal or monoclonal antibodies. The results, identical for both, demonstrate mFNR.1 binding to p55 treated FN coated surfaces increases as a function of the input of p55 suggesting a p55/FN interaction. Thus, p55 inhibits FN binding to BCG and binds directly to FN. Taken together the data show that the purified inhibitory component (p55) from the supernatant of M. vaccae is a FN binding protein.

Because this M. vaccae FN-binding protein had been purified based on its ability to inhibit FN binding to BCG, it was reasonable the BCG should contain a related protein. It was tested whether the polyclonal anti-p55 (made against M. vaccae FN-binding protein) recognized any BCG protein (s). To do this BCG were fractionated into cytosolic and cell wall components as described (Hunter et al., J. Immunol., 142, 2864–2872 (1989)). The crude cell fractions were then subjected to Western blotting with the polyclonal anti-p55. An immunologically crossreactive protein at 55 kD was seen in the cell wall but not the cytosolic fraction from BCG. In addition, a protein at 100 kDa also faintly reacted with the antiserum. Thus, BCG expresses a protein(s) crossreactive with the M. vaccae FN binding protein in the cell wall.

It was tested whether mFNR.1, the mAb anti-p55, could inhibit the binding of intact, viable BCG to FN. mFNR.1 inhibited BCG binding to a FN-coated surface. Thus, an antigenically related protein is necessary for BCG binding to FN.

EXAMPLE 2
Cloning of FAP from M. bovis BCG (FAP-B)

M. bovis BCG DNA (3 µg) was digested with EcoR1, ligated into λZAP Express predigested vector (Stratagene, La Jolla, Calif.) and packaged in vitro using the Gigapack II packaging extracts (Stratagene, La Jolla, Calif.). The use of the EcoRI restriction digest was predetermined by Southern blot. The EcoRI digest yielded a unique 3.5 kilobase (kbp) fragment when probed with a 400 basepair (bp) probe from the FAP-A coding region. The 400 bp probe was obtained by enzymatic digestion of the FAP-A coding region (depicted at Gen Bank accession No. MAU53585) with XbaI and PstI. The packaged DNA was titered and corresponded to $2{,}2\times10^6$ plaque-forming units per ml. Greater than 90% of plaques contained BCG DNA. Approximately 5,000 plaques were transferred onto nitrocellulose filters (Schleicher & Schuell, Keene, N.H.) and screened with a 400 bp PCR product from the FAP-A coding region, which bad been labeled with $^{32}$P according to standard procedures (Schorey et al., *Infect. Immun.,* 63, 2652–2657 (1995)). The blot was hybridized using standard hybridization conditions as described above. The positive plaques were cloned. BCG DNA in these clones were removed from the λ arms using helper phage R408 and ligated into a pBK-CMV phagemid vector (Stratagene).

The isolated clones were digested with EcoRI and resolved on a 1% agarose gel. After DNA transfer to a nitrocellulose filter, the filter was hybridized with the 400 bp PCR fragment from the FAP-A coding region as described above. The positive clone contained the 3.5 kb FAP-B fragment. Digestion of the 3.5 kb insert with PstI yielded three fragments which were subcloned into pBluescript SK vector (Stratagene) to determine the nucleotide sequence. T3 and T7 plasmid primers were used in DNA sequencing. Two individual clones for each fragment were sequenced using the Taq DyeDeoxy Termination Cycle Kit and the Applied Biosystem 373A DNA sequencer (Applied Biosystems, Foster City, Calif.). The nucleotide sequence is shown in SEQ ID NO:1.

The complete FAP-B coding region is 978 nucleotides that encode a 325 amino acid protein with a signal sequence of 39 amino acids (FIG. 1). The predicted amino acid sequence of FAP-B shows similarity to FAP-A and FAP-L (61% and 71%, respectively; Schorey et al., *Mol. Microbiol.,* 21, 321–9 (1996), (Schorey et al., *Infect. Immun.,* 63, 2652–2657 (1995)). Comparison of the amino-terminal sequence of BCG 45/47kDa antigen with FAP-B and *M. tuberculosis* 45/47 kDa antigen indicates that FAP-B corresponds to the BCG 45/47 kDa antigen (Laqueyrerie et al., *Infect. Immun.,* 63, 4003–10 (1995), Romain et al., *Infect. Immun.,* 61, 742–750 (1993)).

EXAMPLE 3

Expression and Purification of the FAP-B

The plasmid containing the 3.5 kb insert was digested with HpaI and EcoRI. The 2.3 kb Hpal-EcoRI fragment containing the FAP-B coding region was ligated into the expression vector pTrcHisB (Invitrogen, San Diego, Calif.), which had been digested with Xhol, blunt ended with Klenow and then digested with EcoRI. To delete the signal peptide and the subsequent 7 amino acids, the clone was digested with KpnI and EcoRI. The resulting 2.1 kb Kpnl-EcoR1 fragment was ligated into pTrcHisC (Invitrogen). The FAP-B fusion proteins contained a domain that included the poly-His tag and was fused to amino acid 47 of SEQ ID NO:2. The amino acid sequence of the domain was MGGSHHHHHHGMASMTGGQQMGRDLYD-DDKHRWIRPRDLQLV (SEQ ID NO:3). The FAP-B fusion proteins were expressed and purified using a $N^{++}$ affinity column under denaturing conditions according to the manufacturer's protocol (Invitrogen). The cell lysates and purified FAP-B were separated by sodium dodecyl sulfate polyacrylamide gel electrophoresis (SDS-PAGE) and visualized by Coomassie Blue staining. After electrophoresis, the antigens were also transferred to a nitrocellulose filter (Schleicher & Schuell), incubated with rabbit anti-FAP polyclonal antibodies.(1:12000 dilution) and then incubated with mouse anti-rabbit IgG-HRP (1,4000 dilution, Sigma Chemical Co., St. Louis, Mo.). The bound HRP was detected with the ECL detection system (Amersham Life Science, Arlington Heights, Ill.).

The complete coding region of FAP-B encodes a protein with a predicted molecular mass of 35.3 kDa. When the full-length FAP-B was expressed in $E.$ $coli$ using the pTrcHisC vector, only low-level expression of FAP-B was obtained. A similarly low expression level of the full length FAF-A sequence was previously recorded (Ratliff et al., Infect. Immun., 61,1889–1894 (1993)). As observed for FAP-A, increased expression was obtained by eliminating the signal sequence. The KpnI-EcoRI FAP-B DNA fragment FAP-B fusion protein does not contain a signal was ligated into the pTrcHisB vector. The resultant FAP-B fusion protein did not contain a signal peptide or the first 7 amino acids of the predicted mature FAP-B protein. The predicted molecular mass of the fusion protein was 35 kDa. Coomassie Blue staining showed this fusion protein migrated as a 50 kDa band on SDS-PAGE. This slow migration may result from its high proline content, which is consistent with previous observations for FA.P-L and FAP-A (Laqueyrerie et at., Infect. Immun., 63, 4003–10 (1995); Ratliff et al., J. Gen. Microbiol., 134, 1307–1313 (1988)). Western bolt showed that rabbit anti-FAP-B polyclonal antibodies reacted with the 50 kDa FAP-B fusion protein as was previously observed fro the FAP-A and FAP-L.

EXAMPLE 4
Attachment of FAP to Fibronectin

Ninety-six-well Immulon II plates (Dynatech, Chantilly, Va.) were coated with 1 μg of human fibronectin (Collaborative Biomedical Products, Bedford, Mass.) or bovine serum albumin (BSA) at 37° C. overnight. Recombinant FAP-B, FAP-A, and β-galactosidase fusion proteins were produced in the pTrcHis vector and purified as described for FAP-B, were biotinylated with NHS-LC-Biotin (Pierce, Rockford, Ill.). Biotinylated FAP-B, FAP-A and β-galactasidase fusion proteins (0.5 μg and 2 μg) were added to wells coated with fibronectin or BSA and incubated at 25° C. for 1 hour. The bound fusion proteins were detected with streptavidin-HRP (1:10,000 dilution; Pierce) and o-phenylenediamine dihydrochloride (Sigma) substrate.

For the fibronectin binding inhibition assay, the plates were coated with 1 μg human fibronectin (Collaborative Biomedical Products, Bedford, Mass.) or BSA. After the plates were incubated with anti-human fibronectin antibodies (1:100 dilution goat anti-fibronectin), anti-FAP-V antibodies (1:100 dilution), or 6 μg FAP-A peptides at 25° C. for 1 hour, biotinylated FAP-B (or FAP-B preincubated with rabbit anti-FAP antibody) was added into each well. The bound biotinylated FAP-B fusion protein was detected with streptavidin-HRP and o-phenylenediamine dihydrochloride substrate. Absorbance was measured at 420 nm.

Figure 3A:
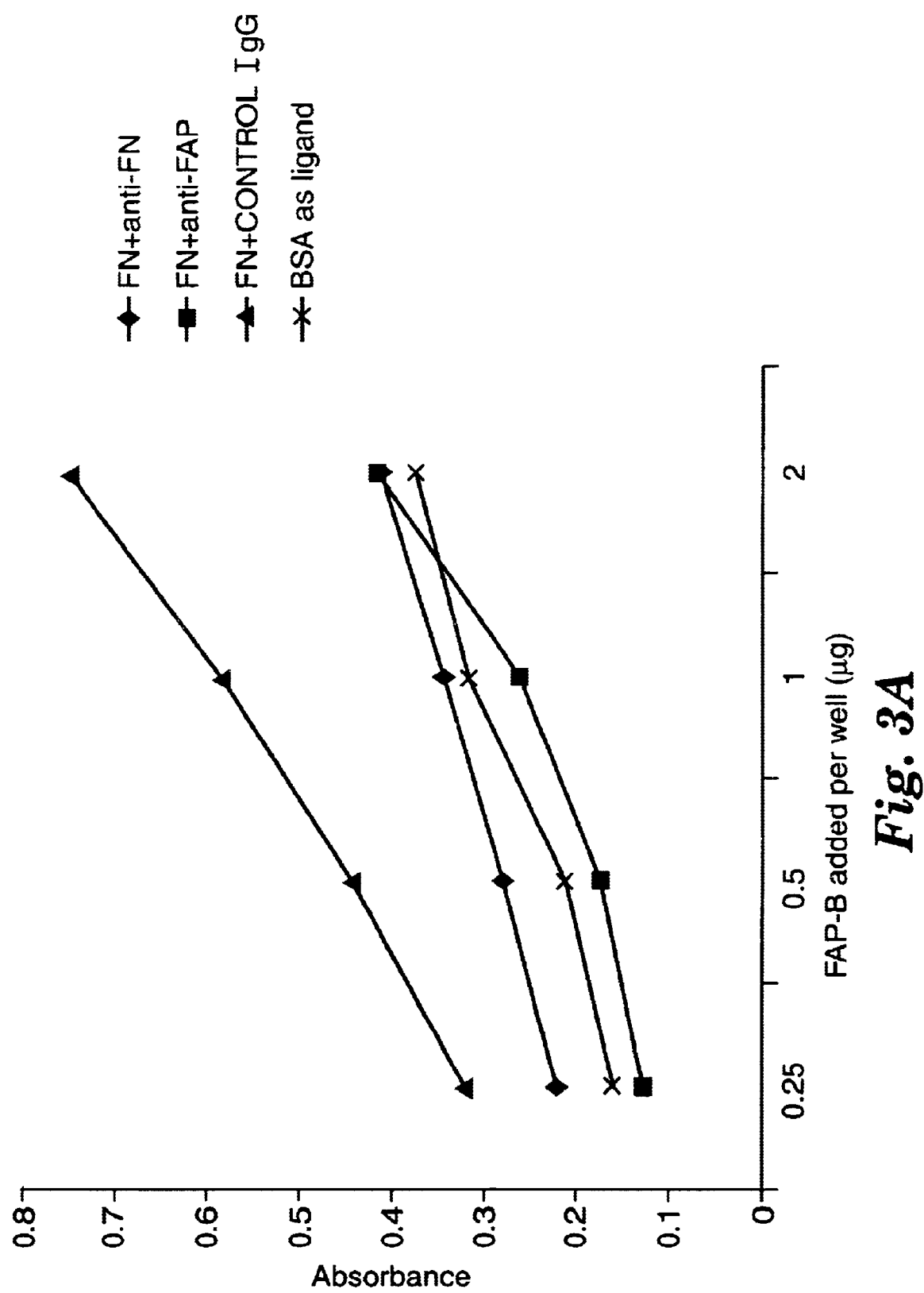
FIG. 3. Effect of anti-fibronectin, anti-FAP, and FAP-$A_{269-292}$ peptide on FAP-B binding to fibronectin (FN). A. Inhibition of FAP-B binding to fibronectin by anti-FN and anti-FAP antibodies. B. Inhibition of FAP-B binding to fibronectin by synthesized FAP-$A_{269-292}$. BSA as ligand, only BSA added to wells; control peptide, the random sequence of the amino acids in the FAP-$A_{269-292}$.
Figure 3B:
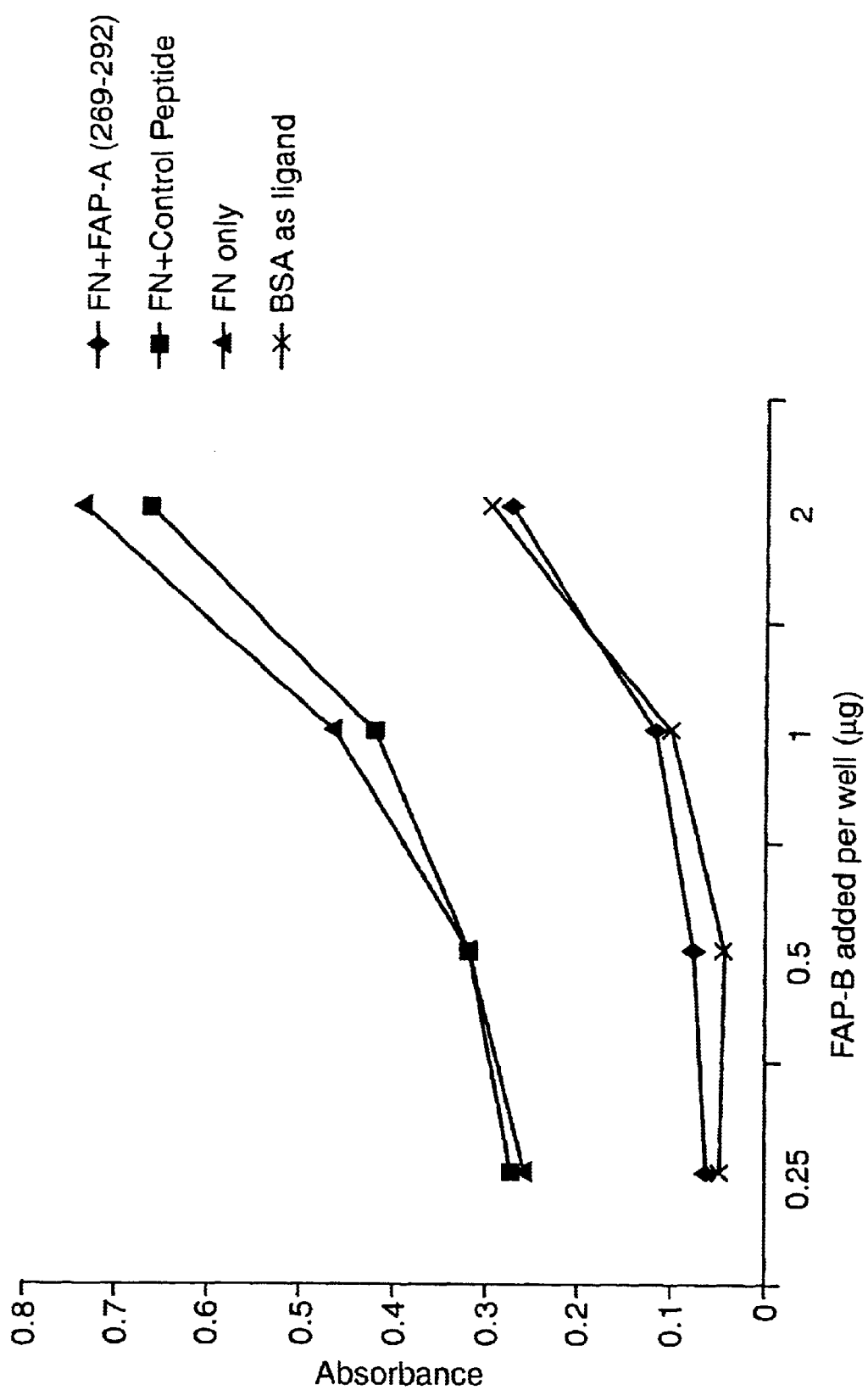

Both purified recombinant FAP-B and FAP-A bound to wells coated with fibronectin. In contrast the control recombinant fusion protein, β-galactosidase, did not bind to fibronectin (FIG. 2). Binding of FAP-B to fibronectin was inhibited by either antibodies to fibronectin or antibodies to FAP-V as previously reported for FAP-L and FAP-A (Ratliff et al., Infect. Immun., 61, 1889–1894 (1993); Schorey et al., Mol. Microbiol., 21, 321–9 (1996); FIG. 3A), Previous studies with FAP-L and FAP-A identified two highly conserved fibronectin binding regions (Ratliff et al., Infect. Immun., 61, 1889–1894 (1993)). One of the regions (amino acids 269–292 in FAP-A and its homologue in FAP-L, amino acids 240–263) was shown to be sufficient to block the attachment of BCG to fibronectin coated surfaces and also BCG attachment to epithelial cells. Since FAP-B also was observed to contain the highly conserved region, the ability of FAP-$A_{269-292}$ to inhibit the attachment of FAP-B to fibronectin was tested as described (Ratliff et al., Infect. Immun., 61, 1889–1894 (1993)). FAP-$A_{269-292}$ and a control peptide consisting of identical amino acids in a randomly ordered sequence were incubated with fibronectin coated wellw for 30 minutes at room temperature prior to the addition of biotinylated FAP-B. FAP-$A_{269-292}$ completely blocked the binding of FAP-B to fibronectin, whereas the corresponding scrambled peptide did not affect binding (FIG. 3B). These data show that FAP-B functions as a fibronectin attachment protein and suggest that the highly conserved binding regions of each FAP are necessary for fibronectin binding.

EXAMPLE 5
FAP-mediated Inhibition of BCG Attachment to Fibronectin

Figure 4:
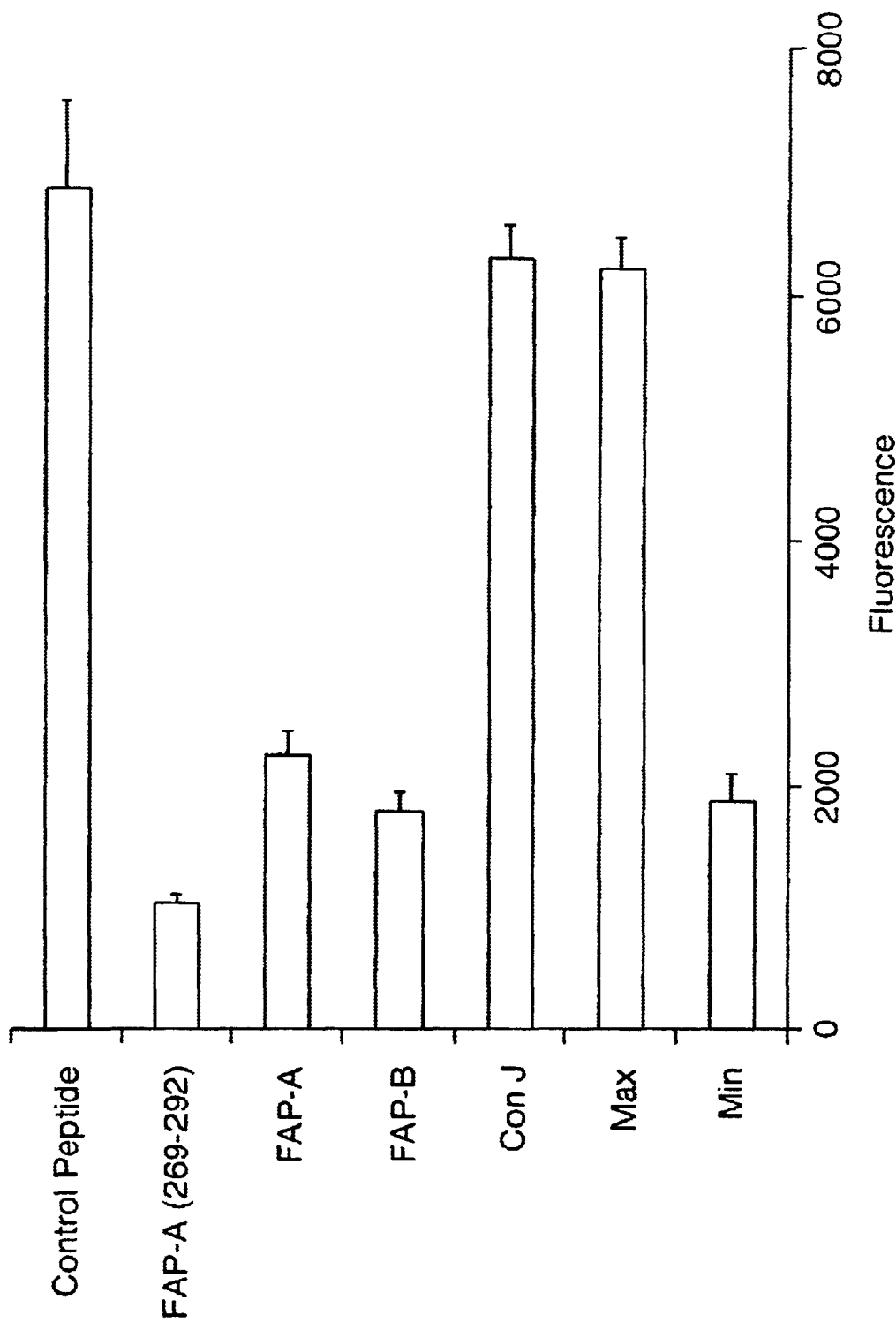
FIG. 4. Effect of FAP-A, FAP-B, and FAP-$A_{269-292}$ on the in vitro attachment of BCG to fibronectin. Max, binding of BCG to fibronectin coated surfaces in the absence of added proteins or peptides; Min, BCG retention on human serum albumin coated surfaces; Control peptide, the random sequence of the amino acids in the FAP-$A_{269-292}$; Con J, control J.

BCG attachment was performed as previously described (Ratliff et al., Infect. Immun., 61, 1889–1894 (1993)). Briefly, Immulon 96 well microtiter plates were coated overnight at 25° C. with 3 μg/ml fibronectin or BSA. After blocking non-specific sites with BSA, a total of $2 \times 10^6$ colony forming units (CFU) of fluorescein isothiacyanate (FITC)-labeled BCG were added in a volume of 50 μl PBS-0.1% BSA. In blocking experiments recombinant FAP-A or FAP-B (1 μM) or inhibitory peptides were added in al volume of 50 μl PBS-0.1% BSA before the addition of BCG. The inhibitory peptides were 1.0 μM control J, which is recombinant thioredoxin produced and purified as described for FAP-A and FAP-B proteins, and 6 μ/ml control peptide. After 90 minutes incubation at 37° C., the wells were washed with PBS and bound FITC-labeled BCG were detected using a Cytofluor 2300 Series System (Millipore, Bedford, Mass.). The ability of FAP-B to inhibit BCG attachment to fibronectin is shown in FIG. 4. These data show that FAP-B, FAP-A, and FAP-$A_{269-292}$ inhibit BCG attachment to fibronectin in an equivalent manner. These data suggest functional equivalence among FAP proteins.

EXAMPLE 6
Prevention of Airway Eosinophilia and Bronchial Hyperreactivity

A murine model of asthma was used to test whether an immune response to the FAP-B protein could induce protection against Th-2 mediated responses such as asthma.

Murine Model of Immunotherapy for Asthma

Figure 5:
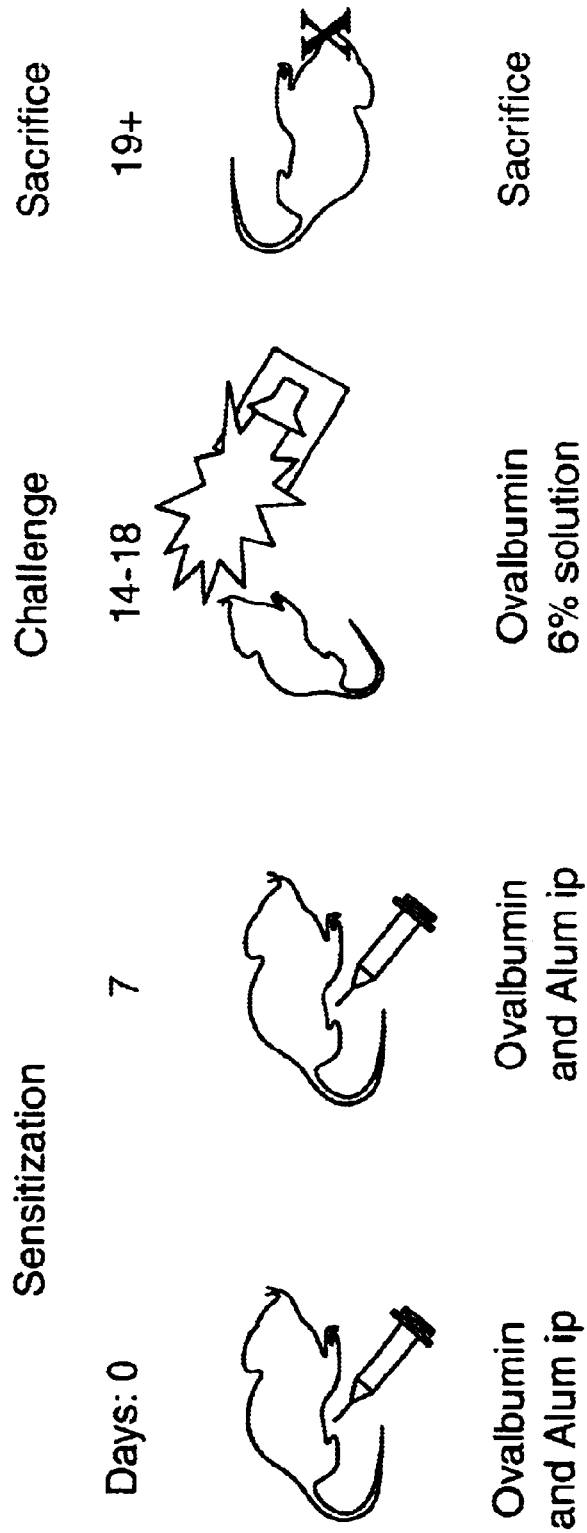
FIG. 5. Ovalbumin murine model of asthma. ip, interperitoneal.

The timing of injections and challenges is depicted in FIG. 5. Female C57BL/6 mice (6–8 week old, Jackson Laboratories) were sensitized to ovalbumin (10 μg, precipitated in alum, in 100 μl PBS) by intraperitoneal injection on days 0 and 7, and subsequently challenged with ovalbumin (6% solution in HBSS) by inhalation (30 minutes daily) on days 14–18. Challenges with ovalbumin were administered by nebulization. Some mice also received FAP-B by intraperitoneal injection prior to sensitization (100 μg, days −1, 0, 6, 7, 14). FAP-B was cloned, expressed, and isolated as described herein. Other (control) mice received FAP-B injections (on the same schedule) without exposure to ovalbumin. Three groups of mice thus received: 1) ovalbumin alone (OVA); 2) FAP-B alone (FAP-B); and 3) both ovalbumin and FAP-B (FAP-B/OVA). All mice underwent assessment of airway reactivity to inhaled methacholine at baseline (Day −1) and prior to sacrifice (Day 19). All mice were sacrificed 24 hours after the final exposure to ovalbumin.

Lung Lavage

Figure 6A:
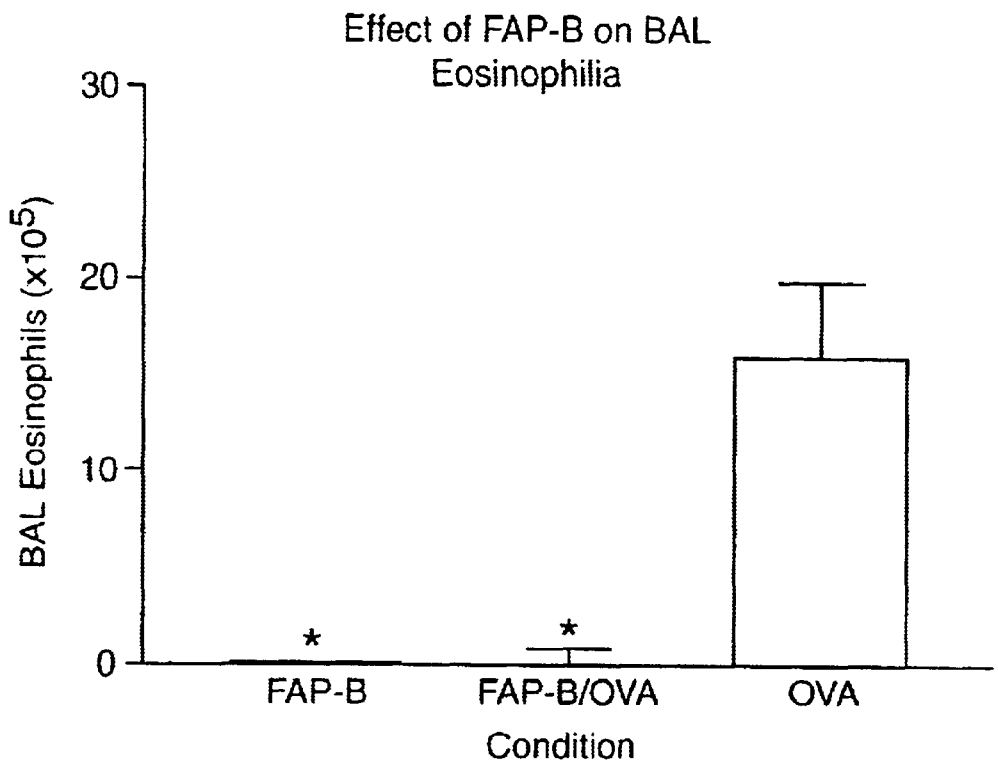
FIG. 6. Lung eosinophilia and cell differential in murine model of asthma in presence or absence of FAP-B. FAP-B, mice that received FAP-B alone and were not sensitized to ovalbumin; FAP-B/OVA, mice that received FAP-B immediately prior to sensitization to ovalbumin; OVA, mice that were sensitized to ovalbumin and did not receive FAP-B. A. Number of eosinophils in lavage fluid. B. Effect of FAP-B on cell differential in lavage fluid. Alv Mac, alveolar macrophages; Ly, lymphocytes; PMN, polymorphonucleocytes; Eo, eosinophils.
Figure 6B:
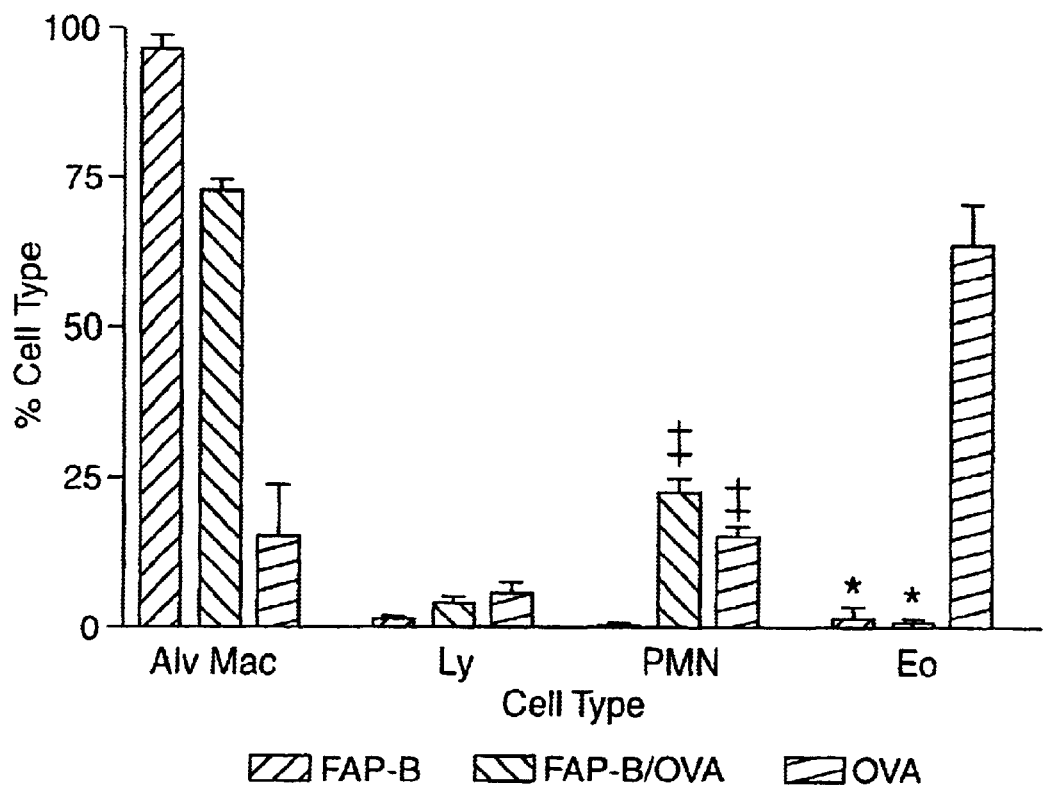

At the time of sacrifice, mice were subjected to whole lung lavage (BAL) to measure cell infiltration. Three milliliters of PBS were administered through a tracheostomy cannula at a pressure of 7-cm $H_2O$, and recovered by gravity flow. Cytospin slide preparations were produced using 15 microliters of BAL, stained using DiffQuik, and total and differential cell counts were performed. Mice that received FAP-B immediately prior to sensitization to ovalbumin developed significantly less BAL eosinophilia than the mice which received ovalbumin, in the absence of any FAP-B, and mice that received FAP-B alone exhibited almost no lung eosinophilia (*p<0.01 vs OVA) (FIG. 6A). Both the FAP-B/OVA mice and the OVA mice developed significant neutrophilia relative to the FAP-B mice (‡p<0.01 vs FAP-B, *p<0.01 vs OVA) (FIG. 6B).

Physiology

Airway hyperreactivity was assessed by methacholine-induced airflow obstruction. Mice were evaluated using a whole body plethysmograph (Buxco, Sharon, Conn.) at the start of the study as well as immediately prior to sacrifice. Measurement was made of respiratory rate, tidal volume, and enhanced pause. Airway resistance is expressed as: $P_{enh}=[(T_e/0.3\ T_r)-1]\times[2\ P_{ef}/3\ P_{if}]$, where $P_{enh}$=enhanced pause, $T_e$=expiratory time (seconds), $T_r$=relaxation time (seconds), $P_{ef}$=peak expiratory flow (ml/sec), and $P_{if}$=peak inspiratory flow (ml/sec). Increasing doses of methacholine (0–100 mg/ml) were administered by nebulization, and $P_{enh}$ was calculated over the subsequent 3 minutes.

Figure 7A:
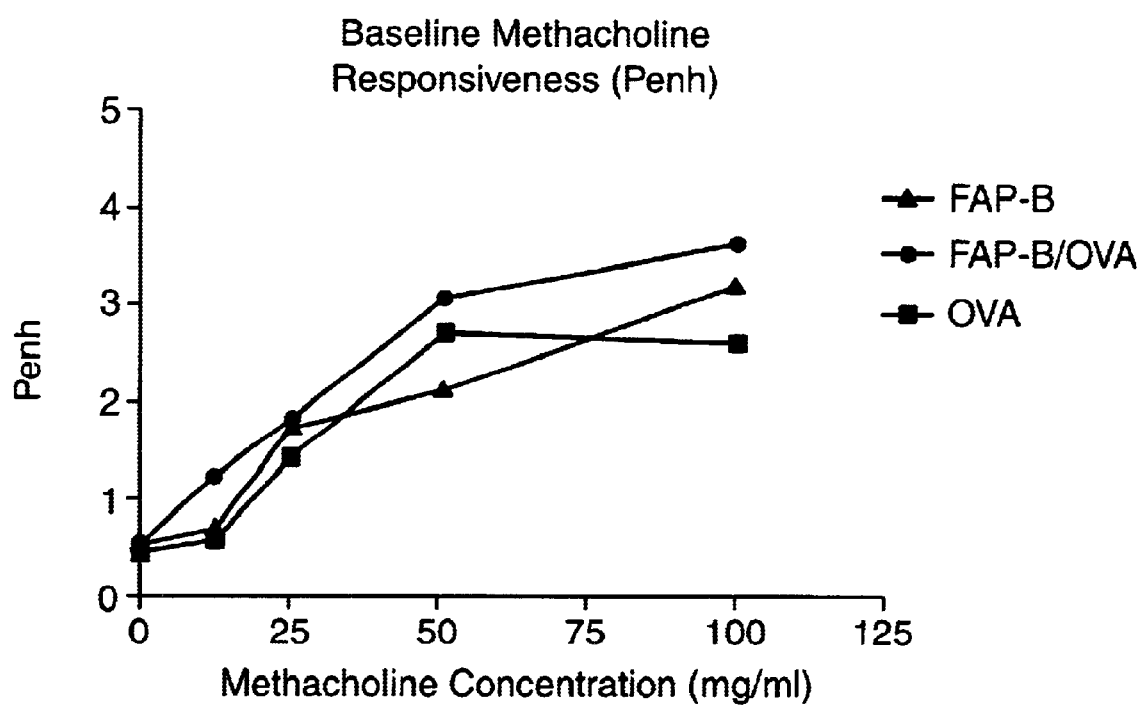
FIG. 7. Airway responsiveness to inhaled methacholine at pre- and post-immunotherapy. FAP-B, mice that received FAP-B alone and were not sensitized to ovalbumin; FAP-B/OVA, mice that received FAP-B immediately prior to sensitization to ovalbumin; OVA, mice that were sensitized to ovalbumin and did not receive FAP-B; Penh, see description in Example 6; baseline, whole body plethysmograph at the start of the study on Day-1; final, whole body plethysmograph at the end of the study. A. Results of whole body plethysmograph of mice in each of the three groups of mice at the start of the study. B. Results of whole body plethysmograph of mice in each of the three groups of mice at the end of the study. C. Methacholine responsiveness in FAP-B mice. D. Methacholine responsiveness in FAP-B/OVA mice. E. Methacholine responsiveness in OVA mice.
Figure 7B:
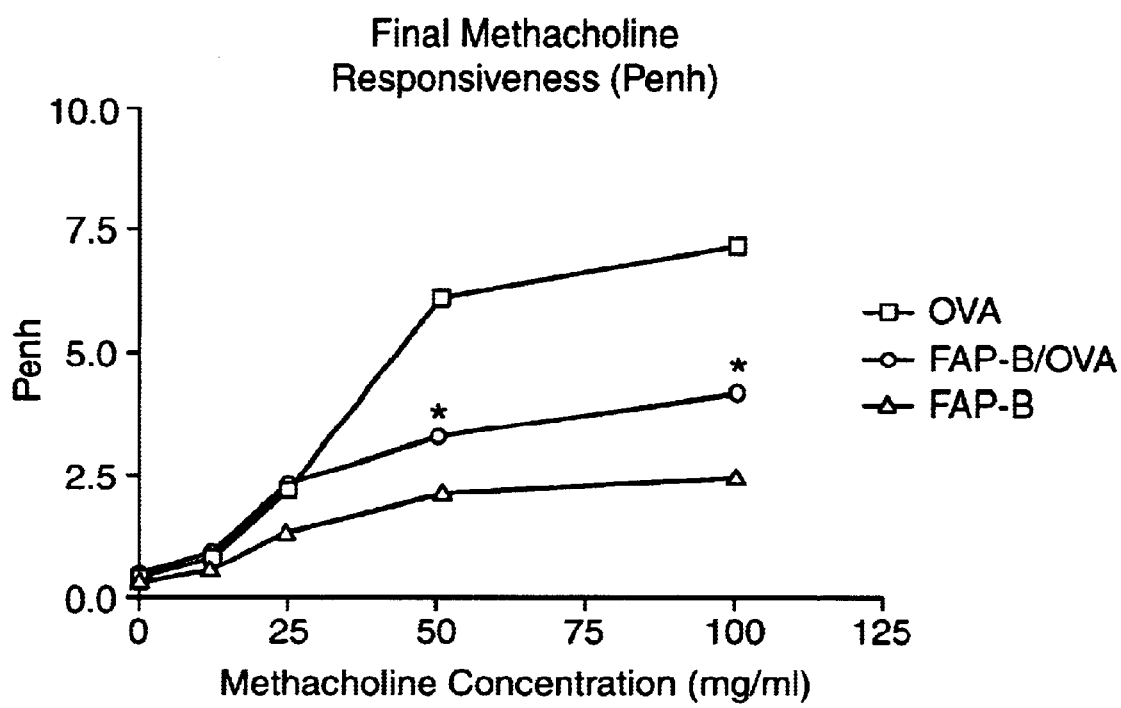
Figure 7C:
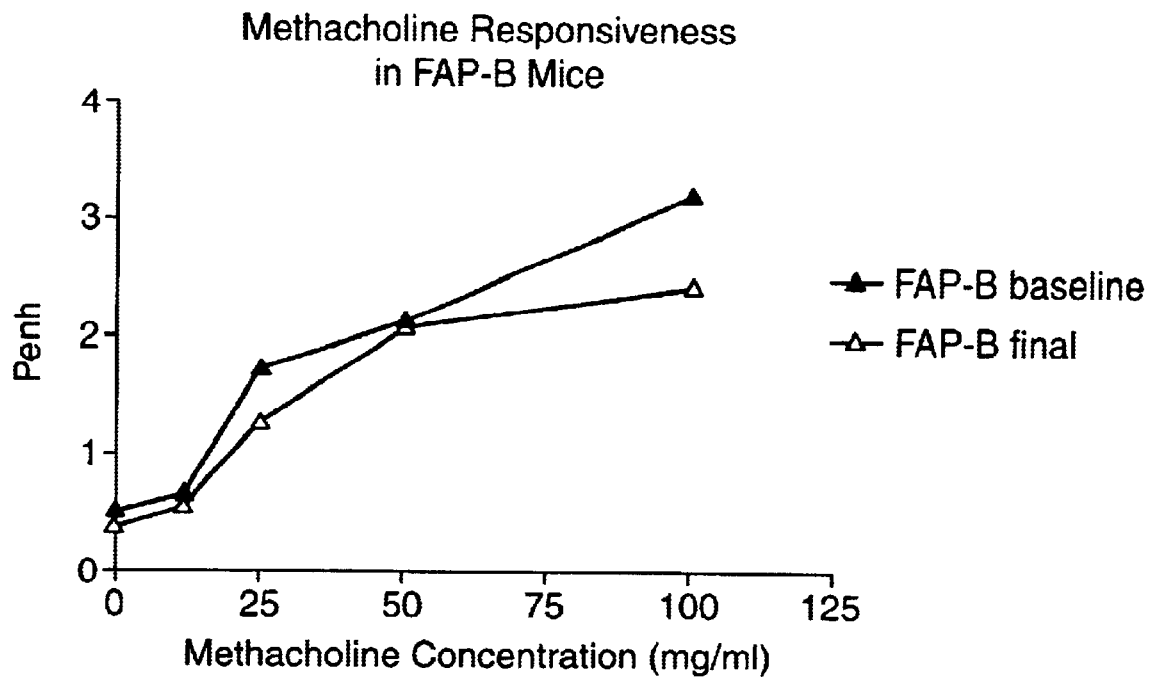
Figure 7D:
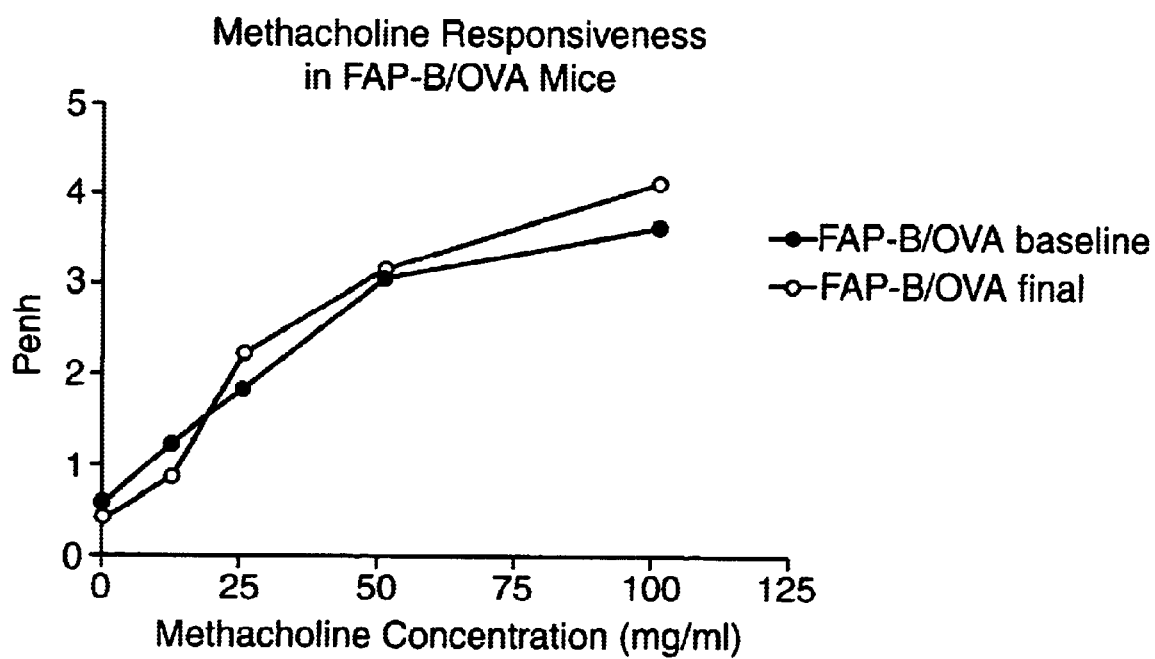
Figure 7E:
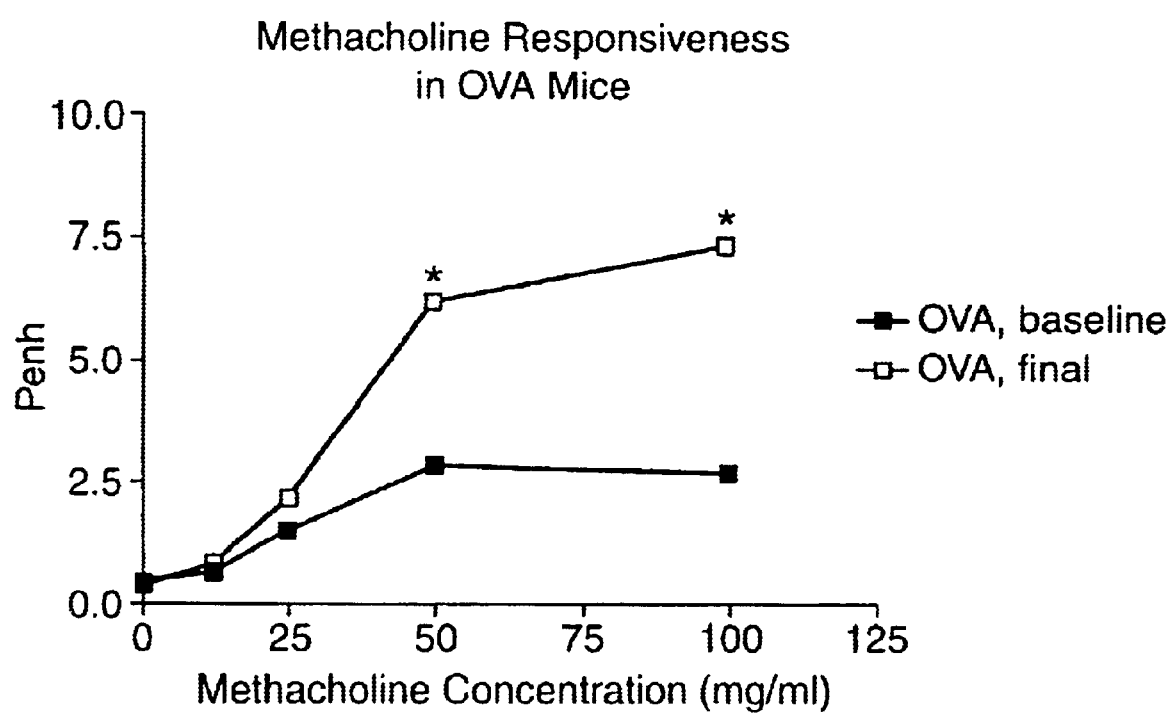
Figure 8:
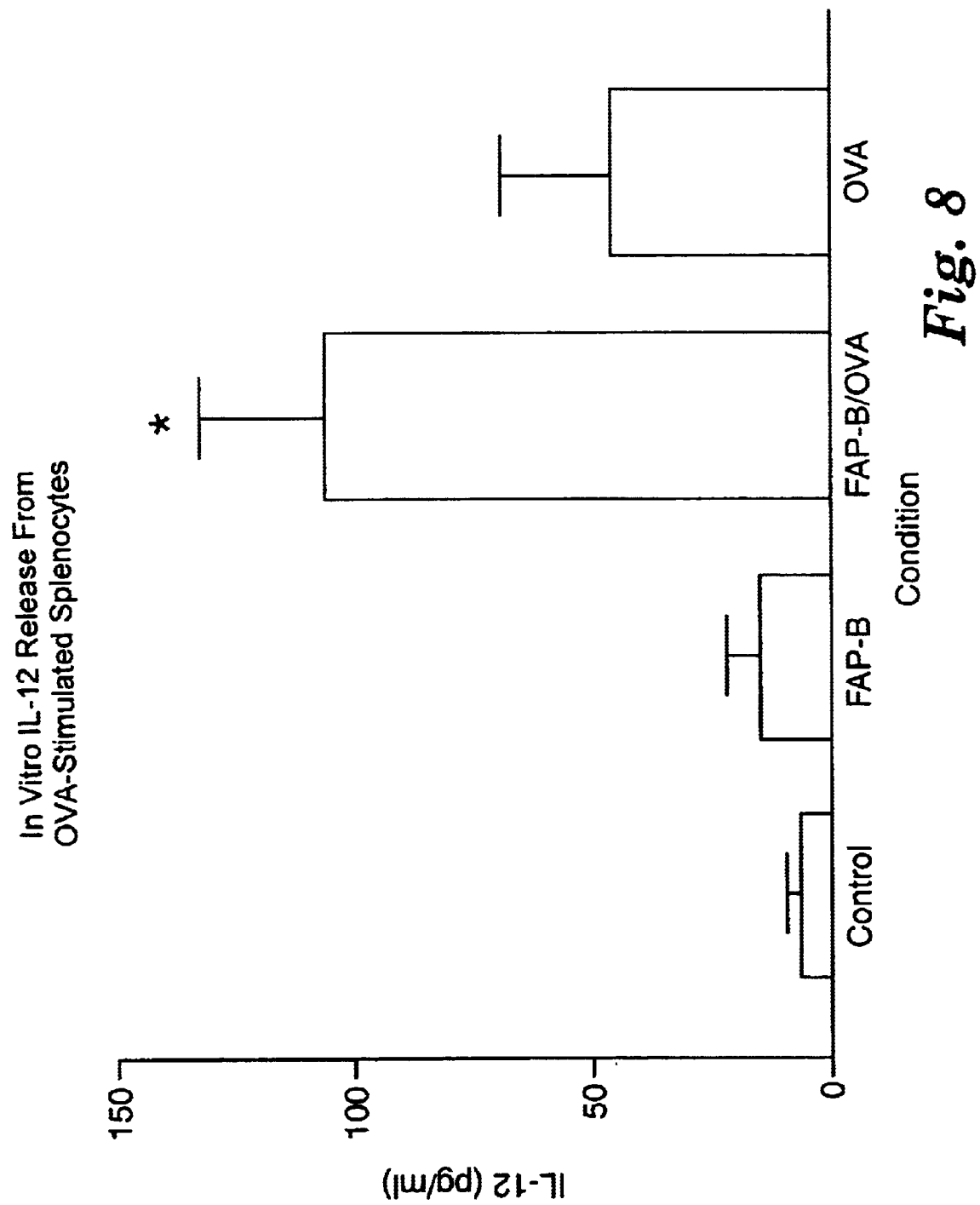
FIG. 8. Antigen-stimulated release of cytokines by murine splenocytes. At the time of sacrifice, splenocytes were isolated from each mouse and cultured in the presence of antigen (ovalbumin, 40 μg/100 μl well). FAP-B, mice that received FAP-B alone and were not sensitized to ovalbumin; FAP-B/OVA, mice that received FAP-B immediately prior to sensitization to ovalbumin; OVA, mice that were sensitized to ovalbumin and did not receive FAP-B; control, mice injected with saline.

At baseline, no significant difference in methacholine responsiveness was detected between the groups (FIG. 7A); following the ovalbumin inhalational challenge, however, the FAP-B/OVA mice were significantly less reactive than OVA mice (FIG. 7B, *p<0.05, vs OVA). There were no differences in responsiveness to inhaled methacholine between the two timepoints in the FAP-B (FIG. 7C) or FAP-B/OVA mice (FIG. 7D), but, following the ovalbumin inhalation, there was a significant increase in $P_{enh}$ response to the higher doses of methacholine in the OVA mice (FIG. 3E).

Splenocyte Culture

In a separate series of experiments, C57BL/6 mice (four/group) were injected with saline (Control), FAP-B (100 μg), ovalbumin (10 μg in alum, OVA), or ovalbumin and FAP-B (FAP-B/OVA) weekly for three weeks. Subsequently, the mice were sacrificed, their spleens were removed en bloc, and splenocytes isolated. Splenocytes were cultured at $2\times10^6$ cells/ml in RPMI-1640 with 10% FCS, 10 mM HEPES, 100 U/ml penicillin and 100 μg/ml streptomycin. Cells were cultured for 24–72 hours in unstimulated conditions or after the addition of ovalbumin (40 μg ovalbumin/100 μl well). Supernatants were harvested at 48 hours, immediately frozen at −70° C., and subsequently batch processed to detect cytokines.

Murine IL-4, IL-12, and IFN-γ were measured using a sandwich ELISA (R&D, Minneapolis, Minn.) according to the manufacturer's instructions. The IL-12 ELISA uses a capture antibody specific to the p70 heterodimer (R&D Systems, Minneapolis, Minn.). Unstimulated splenocytes released no detectable IL-12. Regarding the OVA-stimulated-cells, splenocytes harvested from the FAP-B/OVA group of mice released significantly more IL-12 than the cells from the control, FAP-B, and OVA groups (*p<0.05 vs OVA, <0.01 vs control, FAP-B). There was no detectable differences in release of IL-4 or of IFN-γ.

These data show that FAP-B is an effective immunomodulator in a murine model of atopic asthma, that FAP-B reduces airway eosinophilia as well as bronchial hyperresponsiveness to inhaled methacholine, and that the effects of FAP-B are associated with an induction of antigen-specific release of IL-12. These data also suggest that the immune response to FAP-B may be responsible for the delayed hypersensitivity to mycobacterial antigens.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Sequence Listing Free Text

SEQ ID NO:1 Nucleotide sequence of FAP-B
SEQ ID NO:2 Amino acid sequence of FAP-B
SEQ ID NO:3 Vector-encoded amino terminal domain

What is claimed is:

1. A method for treating at least one symptom of an inflammatory response in a mammal comprising:
   administering an effective amount of an isolated microbial polypeptide to the mammal such that at least one symptom of the inflammatory response is inhibited, wherein the microbial polypeptide comprises an amino acid sequence of SEQ ID NO:2, and wherein the at least one symptom is associated with asthma.

2. A method for treating at least one symptom of an inflammatory response in a mammal comprising administering to the mammal an isolated polypeptide such that at least one symptom of the inflammatory response is inhibited, wherein the polypeptide comprises an amino acid sequence of SEQ ID NO:3 and amino acids 47 to 325 of SEQ ID NO:2, wherein the carboxy terminal amino acid of SEQ ID NO:3 is fused to the amino terminal amino acid of amino acids 47 to 325 of SEQ ID NO:2, and wherein the at least one symptom is associated with asthma.

3. A method for treating at least one symptom of an inflammatory response in a mammal comprising:
   administering an effective amount of an isolated microbial polypeptide to the mammal such that at least one symptom of the inflammatory response is inhibited, wherein the microbial polypeptide comprises amino acids 121 to 283 of SEQ ID NO:2, and wherein the at least one symptom is associated with asthma.

4. The method of claim 3 wherein the amino acid sequence of the microbial polypeptide comprises amino acids 112 to 283 of SEQ ID NO:2.

5. The method of claim 3 wherein the amino acid sequence of the microbial polypeptide comprises amino acids 47 to 325 of SEQ ID NO:2.

6. The method of claim 3 wherein the microbial polypeptide comprises an amino acid sequence of SEQ ID NO:3 and amino acids 47 to 325 of SEQ ID NO:2, wherein the carboxy terminal amino acid of SEQ ID NO:3 is fused to the amino terminal amino acid of amino acids 47 to 325 of SEQ ID NO:2.

7. The method of claim 1 wherein the microbial polypeptide decreases lung eosinophila in the mammal.

8. The method of claim 1 wherein the microbial polypeptide decreases airway hyperactivity in the mammal.

9. The method of claim 2 wherein the polypeptide decreases lung eosinophila in the mammal.

10. The method of claim 2 wherein the polypeptide decreases airway hyperactivity in the mammal.

11. The method of claim 3 wherein the microbial polypeptide decreases lung eosinophila in the mammal.

12. The method of claim 3 wherein the microbial polypeptide decreases airway hyperactivity in the mammal.

* * * * *

UNITED STATES PATENT AND TRADEMARK OFFICE
CERTIFICATE OF CORRECTION

PATENT NO.     : 6,638,518 B1
DATED          : October 28, 2003
INVENTOR(S)    : Ratliff et al.

It is certified that error appears in the above-identified patent and that said Letters Patent is hereby corrected as shown below:

Title page,
Item [56], References Cited, OTHER PUBLICATIONS, please insert
-- Del Prete et al., "IL-4 is an Essential Factor for the IgE Synthesis Induced in vitro by Human T Cell Clones and Their Supernatants," *J. Immunol.*, *140*(12):4193-4198 (1988). --.

Evans et al. reference, delete "1965-184" and insert -- 1965-1984 --.

Romain et al. reference, delete "Kitodalton" and insert -- Kilodalton --.

Column 2,
Line 50, delete "≠" and insert -- - --.

Column 8,
Line 59, delete "parenternal" and insert -- parenteral --.

UNITED STATES PATENT AND TRADEMARK OFFICE
CERTIFICATE OF CORRECTION

PATENT NO.   : 6,638,518 B1  
DATED        : October 28, 2003  
INVENTOR(S)  : Ratliff et al.

It is certified that error appears in the above-identified patent and that said Letters Patent is hereby corrected as shown below:

<u>Column 11,</u>  
Line 49, insert the following paragraph:

--Alternatively, individual organisms, preferably microbes, can be screened for the presence of polypeptides that are capable of inhibiting at least one symptom of an inflammatory response in a mammal. Typically, polypeptides are isolated from an organism and evaluated using the animal model described in Example 6. Once a polypeptide is identified that decreases eosinophilia or decreases responsiveness to inhaled methacholine, the polypeptide can be used in the methods of the present invention, or the polynucleotide sequence encoding the polypeptide can be isolated using methods detailed herein. Organisms, preferably microbes, can also be screened for the presence of polypeptides useful in the present invention by using antibodies prepared against a polypeptide having the amino acid sequence of SEQ ID NO:2, or prepared against a polypeptide having the amino acid sequence depicted at GenBank accession Nos. AAB34676, AAB50543, AAB71842, CAA56555, AAB36458, or P46842. Rabbit polyclonal antibodies against *M. vaccae* FAP (FAP-V) have been prepared that reacted with FAP-B, FAP-A, and FAP-L proteins on Western blots. A monoclonal antibody that can be used is described in U.S. Patent 5,618,916 (Ratliff et al.).--.

Signed and Sealed this

Seventeenth Day of February, 2004

JON W. DUDAS  
*Acting Director of the United States Patent and Trademark Office*